United States Patent
Green et al.

(10) Patent No.: US 7,642,232 B2
(45) Date of Patent: *Jan. 5, 2010

(54) COMPOSITIONS AND METHODS FOR THE PREVENTION AND CONTROL OF INSULIN-INDUCED HYPOGLYCEMIA

(75) Inventors: Daniel T. Green, San Francisco, CA (US); Robert R. Henry, Del Mar, CA (US)

(73) Assignee: DiObex, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/963,584

(22) Filed: Dec. 21, 2007

(65) Prior Publication Data

US 2008/0096801 A1 Apr. 24, 2008

Related U.S. Application Data

(63) Continuation of application No. 10/540,803, filed as application No. PCT/US03/41103 on Dec. 23, 2003, now Pat. No. 7,314,859.

(60) Provisional application No. 60/470,346, filed on May 13, 2003, provisional application No. 60/454,972, filed on Mar. 14, 2003, provisional application No. 60/436,735, filed on Dec. 27, 2002.

(51) Int. Cl.
A61K 38/00 (2006.01)
A61K 51/00 (2006.01)

(52) U.S. Cl. .......................... 514/2; 424/1.69

(58) Field of Classification Search ...................... None
See application file for complete search history.

(56) References Cited

U.S. PATENT DOCUMENTS

| | | | |
|---|---|---|---|
| 2,902,408 A | 9/1959 | Bouman et al. |
| 3,897,551 A | 7/1975 | Bromer |
| 4,003,379 A | 1/1977 | Ellinwood, Jr. |
| 4,492,684 A | 1/1985 | Goosen et al. |
| 4,498,843 A | 2/1985 | Schneider et al. |
| 4,538,616 A | 9/1985 | Rogoff |
| 4,633,878 A | 1/1987 | Bombardieri |
| 4,826,763 A | 5/1989 | Norris et al. |
| 4,839,174 A | 6/1989 | Baker et al. |
| 4,943,435 A | 7/1990 | Baker et al. |
| 5,101,814 A | 4/1992 | Palti |
| 5,190,041 A | 3/1993 | Palti |
| 5,234,903 A | 8/1993 | Nho et al. |
| 5,234,906 A | 8/1993 | Young et al. |
| 5,237,993 A | 8/1993 | Skrabal |
| 5,321,008 A | 6/1994 | Beaumont et al. |
| 5,359,030 A | 10/1994 | Ekwuribe |
| 5,445,832 A | 8/1995 | Orsolini et al. |
| 5,474,552 A | 12/1995 | Palti |
| 5,508,260 A | 4/1996 | Beaumont et al. |
| 5,527,771 A | 6/1996 | Beaumont et al. |
| 5,542,935 A * | 8/1996 | Unger et al. ................. 604/190 |
| 5,637,568 A | 6/1997 | Orsolini et al. |
| 5,643,604 A | 7/1997 | Angeles Uribe et al. |
| 5,643,607 A | 7/1997 | Okada et al. |
| 5,656,590 A | 8/1997 | Rink et al. |
| 5,707,641 A | 1/1998 | Gertner et al. |
| 5,741,211 A | 4/1998 | Renirie et al. |
| 5,814,600 A | 9/1998 | Rink et al. |
| 5,849,322 A | 12/1998 | Ebert et al. |
| 5,869,602 A | 2/1999 | Jonassen et al. |
| 5,919,216 A | 7/1999 | Houben et al. |
| 6,093,167 A | 7/2000 | Houben et al. |
| 6,103,233 A | 8/2000 | Pouletty et al. |
| 6,107,489 A | 8/2000 | Krantz et al. |
| 6,114,304 A | 9/2000 | Kolterman et al. |
| 6,135,978 A | 10/2000 | Houben et al. |
| 6,191,105 B1 | 2/2001 | Ekwuribe et al. |
| 6,197,333 B1 | 3/2001 | Onyuksel et al. |
| 6,217,893 B1 | 4/2001 | Pellet et al. |
| 6,239,107 B1 | 5/2001 | Gozes et al. |
| 6,261,280 B1 | 7/2001 | Houben et al. |
| 6,277,863 B1 | 8/2001 | Krantz et al. |
| 6,284,727 B1 | 9/2001 | Kim et al. |
| 6,319,510 B1 | 11/2001 | Yates |
| 6,329,336 B1 | 12/2001 | Bridon et al. |
| 6,348,214 B1 | 2/2002 | Onyuksel et al. |
| 6,461,331 B1 | 10/2002 | Van Antwerp |
| 6,500,918 B2 | 12/2002 | Ezrin et al. |
| 6,520,326 B2 | 2/2003 | McIvor et al. |
| 6,540,982 B1 | 4/2003 | Adjei et al. |

(Continued)

FOREIGN PATENT DOCUMENTS

EP 0 300 552 1/1989

(Continued)

OTHER PUBLICATIONS

Trading et al. Europ. J. of Pharm. 7 (1969) 206-210 (also cited in IDS of Mar. 20, 2006).*

(Continued)

*Primary Examiner*—Maury Audet
(74) *Attorney, Agent, or Firm*—Townsend and Townsend and Crew LLP

(57) ABSTRACT

Pharmaceutical composition comprising both insulin and glucagon can be administered to control and treat diabetes while reducing or eliminating the risk of insulin-induced hypoglycemia.

13 Claims, 7 Drawing Sheets

U.S. PATENT DOCUMENTS

| | | | |
|---|---|---|---|
| 6,559,122 | B1 | 5/2003 | Oeswein et al. |
| 6,566,490 | B1 | 5/2003 | Maniqub et al. |
| 6,572,542 | B1 * | 6/2003 | Houben et al. ............... 600/300 |
| 6,573,238 | B2 | 6/2003 | Shirley et al. |
| 6,589,548 | B1 | 7/2003 | Oh et al. |
| 6,593,295 | B2 | 7/2003 | Bridon et al. |
| 6,703,365 | B2 | 3/2004 | Galloway et al. |
| 2001/0016643 | A1 | 8/2001 | Jonassen et al. |
| 2001/0033858 | A1 | 10/2001 | Zhang |
| 2002/0026141 | A1 | 2/2002 | Houben et al. |
| 2002/0114829 | A1 | 8/2002 | Onyuksel et al. |
| 2002/0115592 | A1 | 8/2002 | New et al. |
| 2002/0119146 | A1 | 8/2002 | Dupre |
| 2003/0108568 | A1 | 6/2003 | Bridon et al. |
| 2004/0110817 | A1 | 6/2004 | Hulin |
| 2008/0208113 | A1 | 8/2008 | Damiano et al. |

FOREIGN PATENT DOCUMENTS

| | | |
|---|---|---|
| EP | 0442724 | 8/1991 |
| EP | 0684044 | 11/1995 |
| EP | 0816381 | 1/1998 |
| EP | 1264837 | 12/2002 |
| GB | 748857 | 5/1956 |
| GB | 766994 | 1/1957 |
| GB | 766995 | 1/1957 |
| GB | 831907 | 4/1960 |
| GB | 844434 | 8/1960 |
| WO | WO 8809341 | 12/1988 |
| WO | WO 9703688 | 2/1997 |
| WO | WO 9724440 | 7/1997 |
| WO | WO 9808871 | 3/1998 |
| WO | WO 9831383 | 7/1998 |
| WO | WO 9943708 | 9/1999 |
| WO | WO 01/54742 A1 | 8/2001 |
| WO | WO 0182874 | 11/2001 |
| WO | WO 0182981 | 11/2001 |
| WO | WO 0222154 | 3/2002 |
| WO | WO 0232957 | 4/2002 |
| WO | WO 02/43566 A2 | 6/2002 |
| WO | WO 0246227 | 6/2002 |
| WO | WO 04060387 A1 | 7/2004 |
| WO | WO 2004060387 A1 | 7/2004 |

OTHER PUBLICATIONS

Bremer et al. Protein Delivery with Infusion Pumps. Ch. 9, cited in Protein Delivery-Physical Systems, 1997, Plenum Press, pp. 248-249 (also cited in Applicant's IDS of Mar. 20, 2006).*
Abs et al., "Hypoglycemia owing to inappropoiate glucagons secretion treated with a continuous subcutaneous glucagons infusion system," Acta Endocrinol (Copenh), 122(3):319-322 (1990).
American Diabetes Association, "Defining and Reporting Hypoglycemia in Diabetes," Diabetes Care, 28:1245-1249 (2005).
Atvall et al., "Insulin-antagonisitic effects of pulsatile and continuous glucagons infusions in man—a comparison with the effect of adrenaline," J. Clin Endocrinol. Metab., 75(5):1110-1115 (1992).
Aynsley-Green et al., "Nesidioblastosis of the pancreas: definition of the syndrome and the management of the severe neonatal hyperinsulinaemic hypoglycemia," Arch. Dis. Child., 56(7):496-508 (1981).
Beaven et al., European J. Biochem., 11:37-42 (1969).
Bergman et al., "Central role of the adipocyte in the metabolic syndrome," J. Investig. Med., 49(1):119-126 (2001).
Bolli et al., "Abnormal Glucose Counterregulation in Insulin-dependent Diabetes Mellitus, Interaction of Anti-Insulin Antibodies and Impaired Glucagon and Epinephrine Secretion," Diabetes, 32:134-141 (1983).
Bolli et al., "Nocturnal blood glucose control in type I diabetes mellitus," Diabetes Care, 16(suppl. 3):71-89 (1993).
Bratusch-Marrian et al., "The role of 'diabetogenic' hormones on carbohydrate and lipid metabolism following oral glucose loading in insulin dependent diabetics: effect of acute hormone administration," Diabetologia, 21(4):387-393 (1981).
Bray, G.A., "The Zucker-fatty rat: a review," Fed. Proc., 36(2):148-153 (1977).
Bremer et al., "Protein delivery with infusion pumps," Pharm. Biotechnol., 10:239-254 (1997).
Cederblad et al., "Effect of glucagons on glucose production, lipolysis, and gluconeogenesis in familial hyperinsulinism," Horm. Res., 50(2):94-98 (1998).
Chiou et al., "Adjustment of Blood Sugar Levels with Insulin and Glucagons Eyedrops in Normal and Diabetic Rabbits," J Ocul Pharmacol., 6(3):233-41, Fall 1990.
Chiou et al., "Treatment of Hypoglycemia with Glucagon Eye Drops," J Ocul Pharmacol., 4(2):179-86, Summer 1988.
Christiansen et al., "Zinc-protamine-glucagon in the treatment of Paget's disease of bone. Preliminary Report," Acta Med. Scand., 196(6):495-496 (1974).
Chuang et al., "Increase of Blood Glucose Concentrations in Diabetic Patients with Glucagon Eyedrops," Zhongguo Yao Li Xue Bao, 13(3):193-7, May 1992.
Clarke et al., "The effect of hyperglucagonemia on blood glucose concentrations and on insulin requirements in insulin-requiring diabetes mellitus," Diabetes, 27(6):649-652 (1978).
Cryer et al., "Hypoglycemia in Diabetes," Diabetes Care, 26(6):1902-1912 (2003).
Day et al., "Depot-glucagon in the treatment of McArdle's disease," Aust N.Z. J. Med., 15(6):748-750 (1985).
Edelman, "Nocturnal Administration of Very Low Dose Glucagon in Patients with Type 1 Diabetes Reduces Episodes of Nocturnal Hypoglycemia," PowerPoint Presentation at ADA 67th Scientific Sessions, Jun. 22, 2007.
Gerich et al., "Hormonal mechanisms of recovery from insulin-induced hypoglycemia in man," Am. J. Physiol., 236(4):E380-E385 (1979).
Haymond et al., "Mini-Dose Glucagon Rescue for Hypoglycemia in children With Type 1 Diabetes," Diabetes Care, 24(4):643-645 (2001).
Joseph et al., "Oral Delivery of Glucagon-like Peptide-1 in a Modified Polymer Preparation Normalizes Basal Glycaemia in Diabetic db/db Mice," Diabetologia, 43(10):1319-28,Oct. 2000.
Kalima et al., "The effect of zinc-protamine-glucagon in acute pancreatitis," Ann. Chir. Gynaecol., 69(6):293-295 (1980).
Kollee et al., "Persistent neonatal hypoglycaemia due to glucagons deficiency," Arch Dis. Child, 53(5):422-424 (1978).
Lund et al., Proc. Natl. Acad. Sci. USA 79:345-349 (1982).
Miralles et al; "Experience With Intravenous Glucagon Infusions as a Treatment for Resistant Neonatal Hypoglycemia," Arch. Pediatr Adolesc Med., 156(1):999-1004, Oct. 2002.
Muhlhauser et al., "Experience with Intravenous Glucaagon Infusions as a Treatment for Resistant Neonatal Intramuscula, Subcutaneous, and Intravenous Administration," Diabetes Care, 8(1):39-41 Jan.-Feb. 1985.
Paolisso et al., "Pulsatile Rather Than Continuous Glucagon Infusion Leads To Greater Metabolic Derangements In Insulin-Dependent Diabetic Subjects," Diabete Metabl., 1990, Jan.-Feb.; 16(1):42-7 (abstract).
Patzelt et al., "Identification and Processing of Proglucagon in Pancreatic Isklets." Nature, 282:260-266 (1979).
Pillion et al., "Glucagon Administration to the Rat via Eye Drops," J Ocul Pharmacol., 8(4):349-58, Winter 1992.
Pillion et al., "Systemic Absorption of Insulin and Glucagon Applied Topically to the Eyes of Rats and Diabetic Dog," J Ocul Pharmacol Ther., 11(3):238-95, Fall 1995.
Pontiroli et al., "Metabolic Effects of Intranasally Administered Glucagon: Comparison with Intramuscular and Intravenous Injection," Acta Diabetol Lat.22(2):103-10, Apr.-Jun. 1985.
Rosenfalck et al., "Nasal Glucagon in the Treatment of Hypoglycaemia in type 1 (Insulin-Dependent) Diabetic Patients," Diabetes Res Clin Pract. 17(1):43-50 Jul. 1992.
Stenninger et al., "Intranasal Glucagon Treatment Relieves Hypoglycaemia in Children with Type 1 (Insulin-Dependent) Diabetes Mellitus," Diabetologia. 36(10):931-5, Oct. 1993.

Strum et al., Structure-Function Studies on Positions 17, 18, and 21 Replacement Analogues of Glucagon: The Importance of Charged Residues and Salt Bridges on Glucagon Biological Activity, J. Med. Chem. 41:2693-2700 (1998).

Vella et al., "Effect of Glucagon-Like Peptide 1(7-36) Amide on Glucose Effectiveness and Insulin Action in People with Type 2 Diabetes," Diabetes, 49:611617 (2000).

Webb et al., "Glucagon Replacement via Micro-Osmotic Pump Corrects Hypoglycemia and alpha-cell Hyperplasia in Prohome Convertase 2 Knockout Mice," Diabetes 51(2):398-405, Feb. 2002.

Houlbert et al., "Continuous Subcutaneous Infusion of Glucagon by Portable Pump in Non Beta Cell Tumor Hypoglycemia," Diabete & Metab. 11(2):125-7, Apr. 1985.

Trading et al., "Biological and Chemical Properties of Two Glucagon Preparations with Prolonged Action," Eur. J. Pharmacology, 7:206-210 (1969).

Examination Report for European Application No. 03 814 932.4-1521 (Jun. 10, 2009).

Jouhaneau, "Glucagon And Insulin Oscillatory Self-Administration in Rats", Physiology & Behavior, 23(1):31-33, (1979).

El-Khatib, Ph.D., et al., "A feasibility study of bihormonal closed-loop blood glucose control using dual subcutaneous infusion of insulin and glucagon in ambulatory diabetic swine," Journal of Diabetes Science a and Technology, Jul. 2009, pp. 1-15, vol. 3, Issue 4.

El-Khatib, Ph.D., et al., "Adaptive closed-loop control provides blooc-glucose regulation using dual subcutaneous insulin and glucagon infusion in diabetic swine," Journal of Diabetes Science and Technology, Mar. 2007, pp. 181-192, vol. 1, Issue 2.

El-Khatib, Ph.D., et al., "Pharmacodynamics and stability of subcutaneously infused glucagon in a type 1 diabetic swine model in vivo," Dabetes Technology & Therapeutics, 2007, pp. 135-144, vol. 9, No. 2.

Liljenquist et al., "Effects of glucagon on lipolysis and ketogenesis in normal and diabetic men," The Journal of Clinical Investigation, Jan. 1974, pp. 190-197, vol. 53.

Marliss, M.D., et al., "Normalization of glycemia in diabetics during meals with insulin and glucagon delivery by the artificial pancreas," Diabetes, Jul. 1977, pp. 663-672, vol. 26, No. 7, New York, NY.

Shichiri et al., "Closed-loop glycemic control with a wearable artificial endocrine pancreas," Diabetes, Dec. 1984, pp. 1200-1202, vol. 33, New York, NY.

File History of U.S. Appl. No. 11/169,825, filed Jun. 28, 2005.
File History of U.S. Appl. No. 11/927,513, filed Oct. 29, 2007.
File History of U.S. Appl. No. 11/927,535, filed Oct. 29, 2007.
File History of U.S. Appl. No. 11/927,587, filed Oct. 29, 2007.
File History of U.S. Appl. No. 11/927,621, filed Oct. 29, 2007.

Abs et al., "Hypoglycemia owing to inappropriate glucagons secretion treated with a continuous subcutaneous glucagons infusion system," Acta Endocrinol (Copenh), 122(3):319-322 (1990).

American Diabetes Association, "Defining and Reporting Hypoglycemia in Diabetes," Diabetes Care, 28:1245-1249 (2005).

Atvall et al., "Insulin-antagonistic effects of pulsatile and continuous glucagons infusions in man——a comparison with the effect of adrenaline," J. Clin Endocrinol. Metab., 74(5):1110-1115 (1992).

Aynsley-Green et al., "Nesidioblastosis of the pancreas: definition of the syndrome and the management of the severe neonatal hyperinsulinaemic hypoglycemia," Arch. Dis. Child., 56(7):496-508 (1981).

Banarer et al., "Intraislet Hyperinsulinemia Prevents the Glucagon Response to Hypoglycemia Despite an Intact Autonomic Response," Diabetes, 51:958-965 (2002).

Beaven et al., European J. Biochem., 11:37-42 (1969).

Bergman et al., "Central role of the adipocyte inthe metabolic syndrome," J. Investig. Med., 49(1):119-126 (2001).

Bolli et al., "Abnormal Glucose Counterregulation in Insulin-dependent Diabetes Mellitus, Interaction of Anti-Insulin Antibodies amd Impaired Glucagon and Epinephrine Secretion," Diabetes, 32:134-141 (1983).

Bolli et al., "Nocturnal blood glucose control in type I diabetes mellitus," Diabetes Care, 16(suppl. 3):71-89 (1993).

Bratusch-Marrian et al., "The role of 'diabetogenic' hormones on carbohydrate and lipid metabolism following oral glucose loading in insulin dependent diabetics: effect of acute hormone administration," Diabetologia, 21(4):387-393 (1981).

Edelman, "Nocturnal Administration of Very Low Dose Glucagon in Patients with Type 1 Diabetes Reduces Episodes of Nocturnal Hypoglycemica," PowerPoint Presentation at ADA 67th Scientific Sessions, Jun. 22, 2007.

Fabris et al., Nasal Administration of Glucagon in the Treatment of Neonatal Hypoglycemia, Minevraa Pediatr. 36⊗0):525-8, May 31, 1984.

Gamba et al., "Zinc protamine glucagons in refractory heart faliure with arrhythimia," Minerva Med., 68(53:3613-3626 (1977) article in Italian.

Gerich et al., "Hormonal mechanisms of recovery from insulin-induced hypoglycemia in man," Am. J. Physiol., 236(4):E380-E385 (1979).

Haymond et al., "Mini-Dose Glucagon Rescue for Hypoglycemia in children With Type 1 Diabetes," Diabetes Care, 24(4):643-645 (2001).

Ivokovic-Lazar, T., "Development and differentiation od adipose tissue," Med, Pregl., 56(3-4):142-145 (2003), abstract, article in Croatian.

Joseph et al., "Oral Delivery of Glucagon-like Peptide-1 in a Modified Polymer Preparation Normalizes Basal Glycaemia in Diabetic db/db Mice," Diabetologia, 43(10):1319-28, Oct. 2000.

Kaindl et al., "Heart therapy using zinc protamine glucagons," Verh Dtsch Ges Inn Med., 78:1099-1101 (1972) article in German.

Kaindl et al., "Zinc-protamine-glucagon in the therapy of heart failure," Z Gesamte Inn Med., 27(24):1097-1098 (1972) article in German.

Kalima et al., "The effect of zinc-protamine-glucagon in acute pancreatitis," Ann. Chir. Gynaecol., 69(6):293-295 (1980).

Kollee et al., "Persistent neonatal hypoglycaimia due to glucagons deficiency," Arch Dis. Child, 53(5):422-424 (1978).

Lund et al., Proc. Natl. Acad. Sci. USA 79:345-349 (1982).

Miralles et al; "Experience With Intravenous Glucagon Infusions as a Treatment for Resistant Neonatal Hypoglycemia," Arch. Pediatr Adolesc Med., 156(1):999-1004, Oct. 2002.

Muhlhauser et al., "Experience with Intravenous Glucaagon Infusions as a Treatment for Resistant Neonatal Intramuscula, Subcutaneous, and Intravenous Administration," Diabetes Care, 8(1):39-41 Jan.-Feb. 1985.

Nicolaidis, S., "Physiology of food intake and regulation of body weight," Ann. Endocrinol., 49(2):89-97 (1988) abstract, article in French.

Paolisso et al., "Pulsatile Rather Than Continuous Glucagon Infusion Leads to Greater Metabolic Derangements in Insulin-Dependent Diabetic Subjects," Diabete Metabl., 1990, Jan.-Feb.; 16(1):42-7 (abstract).

Patzelt et al., "Identification and Processing of Proglucagon in Pancreatic Isklets." Nature, 282:260-266 (1979).

Pichler et al., "Haemodynamic effects of depot zinc protamine glucagons in heart failure," Wein Klin Wochenschr., 91(2):49-51 (1979) abstract only, article in German.

Pillion et al., "Glucagon Administration to the Rat via Eye Drops," J Ocul Pharmacol., 8(4):349-58, Winter 1992.

Pillion et al., "Systemic Absorption of Insulin and Glucagon Applied Topically to the Eyes of Rats and Diabetic Dog," J Ocul Pharmacol Ther., 11(3):238-95, Fall 1995.

Pontiroli et al., "Metabolic Effects of Intranasally Administered Glucagon: Comparison with Intramuscular and Intravenous Injection," Acta Diabetol Lat.22(2):103-10, Apr.-Jun. 1985.

Rosenfalck et al., "Nasal Glucagon in the Treatment of Hypoglycaemia in type 1 (Insulin-Dependent) Diabetic Patients," Diabetes Res Clin Pract. 17(1):43-50 Jul. 1992.

Schmid et al., "McArdie's disease: therapeutic use of depot-glucagon," Dtsch Med. Wochenschr., 107(47):1809-1811 (1982) abstract only, article in German.

Stenninger et al., "Intranasal Glucagon Treatment Relieves Hypoglycaemia in Children with Type 1 (Insulin-Dependent) Diabetes Mellitus," Diabetologia. 36(10):931-5, Oct. 1993.

Sturm et al., "Structure-Function Studies on Positions 17, 18, and 21 Replacement Analogues of Glucagon: the Importance of Changed Resisdues and Salt Bridges on Glucagon Biological Activity," J. Med. Chem. 41:2693-2700 (1998).

Vella et al., "Effect of Glucagon-like Peptide 1(7-36) Amide on Glucose Effectiveness and Insulin Action in Peptide with Type 2 Diabetes," Diabetes, 49:611617 (2000).

Wedd et al., "Glucagon Replacement via Micro-Ocmotic Pump Corrects Hypoglycemia and alpha-cell Hyperplasia in Prohome Convertase 2 Knockout Mice," Diabetes 51(2):398-405, Feb. 2002.

Houlbert et al., "Continuous Subcutaneous Infusion of Glucagon by Portable Pump in Non Beta Cell Tumor Hypoglycemia," Diabete & Metab. 11(2):125-7, Apr. 1985.

Trading et al., "Biological and Chemical Properties of Two Glucagon Preparations with Prolonged Action," Eur. J. Pharmacology, 7:206-210.

Examination Report for European Application No. 03 814 932.4-1521 (Jun. 10, 2009).

De Galan et al. "Pathophysiology and management of recurrent hypoglycemia and hypoglycemia unawareness in diabetes," *Netherlands Journal of Medicine*, 64(8): 269-279 (2006).

Edelman et al. "Subcutaneous infusion of very low dose-glucagon averts insulin induced hypoglycemia in patients with type 1 diabetes mellitus," *Diabetologia*, 49 (Suppl. 1): 506 (2006).

Fanelli et al. "Glucagon: the effects of its excess and deficiency on insulin action." *Nutrition, Metabolism, and Cardiovascular Diseases: NMCD*, 16, suppl. 1, pp. S28-S34 (2006).

Isley et al. "Very low dose glucagon averts insulin induced hypoglycemia in patients with type 1 diabetes," *Diabetes*, 55 (Suppl. 1): A117 (2006).

Supplementary European Search Report dated Aug. 6, 2009, received in European Application No. 05787795.

* cited by examiner

COMPOSITIONS AND METHODS FOR THE PREVENTION AND CONTROL OF INSULIN-INDUCED HYPOGLYCEMIA

This application is a continuation of application Ser. No. 10/540,803, filed Dec. 14, 2005, now issued as U.S. Pat. No. 7,314,859. Application Ser. No. 10/540,803 was a national phase application of PCT/US2003/041103, filed Dec. 23, 2003, which claimed benefit of U.S. provisional patent application Nos. 60/436,735 (filed Dec. 27, 2002), 60/454,972 (filed Mar. 14, 2003) and 60/470,346 (filed May 13, 2003). The entire contents of each of the afore-listed applications is incorporated herein by reference.

FIELD OF THE INVENTION

The present invention relates to the fields of biology, pharmacology, and medicine.

BACKGROUND OF THE INVENTION

Insulin is produced by the beta cells and glucagon by the alpha cells of the Pancreatic Islets of Langerhans. One of insulin's major effects is to lower blood glucose by suppressing hepatic glucose output and stimulating peripheral glucose uptake. Endogenous insulin levels may be low or undetectable in some patients with diabetes mellitus. Exogenous insulin is usually administered to reduce hyperglycemia in situations where circulating insulin levels are either low or ineffective. Glucagon generally has effects opposite to those of insulin, including, primarily, increasing hepatic glucose output and thereby increasing blood sugar levels. Glucagon levels tend to increase when blood glucose levels fall to abnormally low levels, particularly in patients who utilize exogenous insulin.

Current goals for diabetes management include near normal blood glucose levels to delay or prevent microvascular complications; achievement of this goal usually requires intensive insulin therapy. In striving to achieve this goal, physicians have encountered a substantial increase in the frequency and severity of hypoglycemia in their diabetic patients.

Hypoglycemia, characterized by low blood sugar levels, results in autonomic and adrenergic, as well as neuroglycopenic, symptoms; these symptoms typically are encountered as a result of inadvertent excessive insulin administration. Some patients with diabetes may be unable to sense low blood glucose accurately due to hypoglycemic unawareness. Hypoglycemia and the conditions that can result from a lack of awareness of its presence are serious complications of chronic insulin therapy and can occur due to the impaired counter-regulatory (anti-insulin) responses in diabetic patients. One of the major counter-regulatory hormones that normally responds to hypoglycemia is glucagon. Not infrequently, the glucagon response to acute hypoglycemia is impaired or lost in patients with advanced Type 1 and Type 2 diabetes.

Thus, there remains a need for new methods to treat diabetes that are less likely to induce hypoglycemia than current insulin therapies. The present invention meets this need.

SUMMARY OF THE INVENTION

In a first embodiment, the present invention provides pharmaceutical compositions comprising both insulin and glucagon in amounts that can be administered to a diabetic patient not only to achieve therapeutically effective control of diabetes but also to prevent hypoglycemia. The formulations of the invention include formulations suitable for injection, formulations suitable for administration orally, formulations suitable for transdermal administration, formulations suitable for ocular administration, and formulations suitable for inhalation.

In a second embodiment, the present invention provides methods to treat diabetes in a human or other mammal without inducing hypoglycemia, which comprise co-administration of insulin and glucagon, wherein said insulin is administered in amounts therapeutically effective for the control of diabetes, and said glucagon is administered in amounts therapeutically effective for the prevention of hypoglycemia, and wherein both insulin and glucagon are administered simultaneously with one another or within about less than four hours of each other (as when regular, LISPRO, and ASPART insulins are used) or within less than about six to twelve hours of each other (as when longer acting insulins are used), and in any event prior to the onset of clinically observable hypoglycemia.

In a third embodiment, the present invention provides a method to maintain blood glucose levels in a range that is neither hyperglycemic nor hypoglycemic which comprise co-administration of insulin and glucagon.

In a fourth embodiment, the present invention provides glucagon formulations and modified glucagon suitable for co-administration with insulin in accordance with the methods of the present invention.

DETAILED DESCRIPTION OF THE INVENTION

Figure 1:
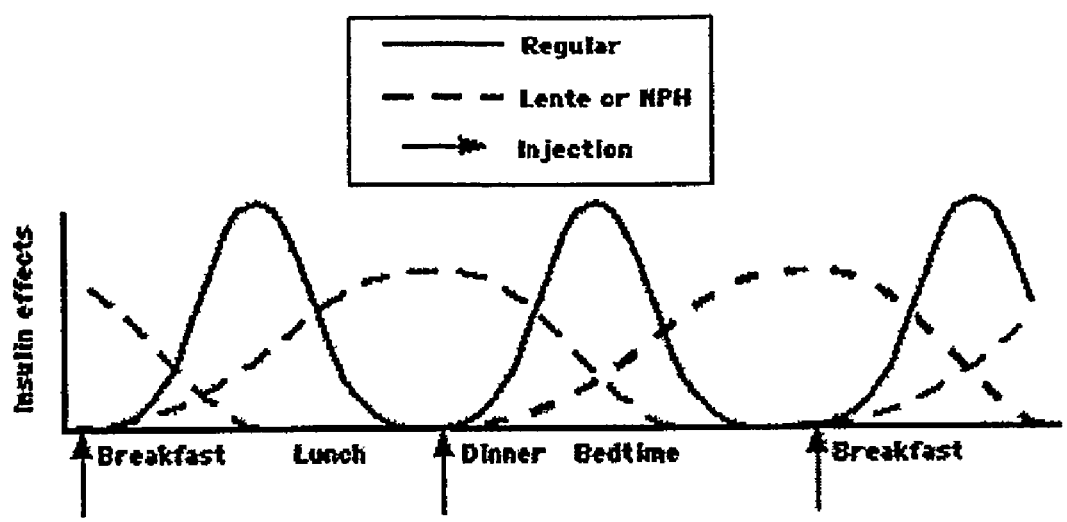
FIG. 1 is a graph illustrating idealized pharmacokinetics for a mixture of regular and intermediate acting insulin. The graph shows the effect of a twice-daily insulin regimen: Twice-daily administration of regular (solid lines) and intermediate-acting LENT or NPH (dashed lines) insulins before breakfast and the evening meal provides peaks of insulin after the injections as well as a relatively constant baseline level of insulin throughout the day after injections of the intermediate-acting insulins.

The present invention provides methods and compositions that can prevent, or significantly reduce the frequency and severity of, hypoglycemia in insulin-treated diabetic patients (both Type 1 and 2). The methods and compositions of the invention can be used to replenish or restore the abnormally low glucagon responses often coincident with insulin administration, thereby preventing hypoglycemia. The invention, in one aspect, provides pharmaceutical formulations of two hormones, insulin and glucagon, combined in molar ratios that optimize glycemic management and attenuate the incidence of or prevent hypoglycemia. In another aspect, the invention provides methods and compositions for the simultaneous but separate administration of insulin and glucagon to achieve this benefit. While the simultaneous administration of two hormones with activities viewed as counteracting would appear to have no beneficial effect, the present invention arises in part from the counterintuitive realization that such administration achieves the beneficial effect of preventing hypoglycemia by virtue of the buffering or blunting effects of glucagon without diminishing the beneficial effects of glucose regulation provided by insulin.

Thus, the present invention provides a method for controlling diabetes with a reduced risk of hypoglycemia by simultaneous administration of insulin and glucagon to a diabetic patient. In one aspect, the invention provides a method of preventing hypoglycemia in a diabetic patient who is being treated with insulin and who is not suffering hypoglycemic symptoms, by administering glucagon to the patient in an amount therapeutically effective for the prevention of hypoglycemia. In an embodiment, the glucagon is administered simultaneously with, or within one minute to four hours after said patient has last been administered insulin.

As will be apparent to one of skill in the art upon consideration of the disclosure herein, any of the many different forms of insulin, as well as any of the many different routes of administration of insulin, including those both approved by the FDA and in development, can be used in the methods and formulations of the invention. Moreover, any of the currently available formulations of glucagon can similarly be used in the methods and formulations of the invention. Importantly, however, because glucagon has been, prior to the present invention, administered only parenterally to control hypoglycemia, the present invention provides new glucagon derivatives and new formulations of and methods of administering glucagon that are particularly suited to achieve the benefits provided by the present invention, including delayed and/or extended action glucagon.

While the precise dosage of insulin and glucagon will vary from patient to patient and depend upon a variety of factors, including but not limited to age and sex of the patient, type and severity of diabetes, past history of the patient, including hypoglycemic and hyperglycemic episodes, type of insulin and glucagon employed, and the like, the beneficial effects of the invention can generally be achieved by administering both insulin and glucagon in the ratio of 1 unit of Insulin to 0.02-40 milliunits of glucagon (0.02 to 40 micrograms). In a preferred embodiment, the ratio is 1 unit of insulin to 0.2 to 4.0 milliunits of glucagon (0.2 to 4.0 micrograms).

As noted above, the benefits of the present invention can be achieved by administration of any of the currently available forms of insulin, including but not limited to recombinant human soluble (regular) insulin, human insulin analogs, animal insulins, derived, for example, from beef, pork and other species, as well as delayed release forms, including intermediate and long acting insulin. Moreover, any of the currently used routes of administration, as well as newer routes in development, can be employed, including but not limited to subcutaneous, intramuscular, and intravenous injection, as well as oral, buccal, nasal, transdermal, and pulmonary airway administration. Typical doses and dose ranges for the administration of insulin to control diabetes known in the art are suitable for use in the methods and compositions of the invention.

For example, prandial short-acting insulins, such as regular insulin and the LISPRO and ASPART derivatives thereof, are well known in the art and commonly used to treat diabetes. Such insulins can be used to illustrate the invention in a manner applicable to other forms, including but not limited to NPH, LENTE, SEMI-LENTE, DETEMIR, ULTRA-LENTE, and GLARGINE (LANTUS), and pre-mixed formulations of regular and long-acting insulins. In this illustration, the molecular weights ascribed to all three of these prandial short-acting insulins are similar, with LISPRO at 5808, ASPART at 5825.8 and regular insulin at 5807, and the molecular weight ascribed to glucagon is 3483.

The usual range of prandial insulin injections in Type 1 diabetes can be approximated as two standard deviations from the mean, resulting in an insulin dose range of 2-20 units. More than 95% of Type 1 diabetics will be administered a prandial insulin dose within this range. The three prandial insulins noted above all achieve peak serum concentrations within 1-2 hours after subcutaneous administration and have a duration of about 5 hours.

Currently, hypoglycemia is treated by a single parenteral injection of glucagon in a dose of about 1 mg (1 unit); this dose is a gross excess of the dose actually required to control hypoglycemia. When glucagon is given subcutaneously or intramuscularly, serum glucagon peaks within an hour, and its effects can persist for several hours.

It has been discovered, based in part on the respective times to peak serum level and durations of action of the prandial insulins and subcutaneously administered glucagon, that there is a mismatch between subcutaneous insulin and glucagon pharmacokinetics. The present invention provides longer-acting glucagon formulations and derivatives that can be used to correct this mis-match, where desired or of benefit to the patient. "Longer-acting" glucagon has a half-life greater than that of standard glucagon (natural extract or rDNA produced synthetic glucagon).

To provide the dose of glucagon required if the duration of effect is to be more similar to that of the prandial insulins, one can use a dose that approximates the basal replacement dose. The usual basal glucagon replacement dose by IV infusion is 0.5-0.75 ng/kg/min; one can assume that a wider range of glucagon infusions, from as low as 0.10 to 5.00 ng/kg/min (more often, 0.10 to 3.00 ng/kg/min) can be effective, depending on the patient, the insulin dose, and other factors. To match the PK of the insulins, these glucagon infusion rates would be administered for a period of time ranging from 150 minutes to 300 minutes. One can then multiply the replacement rates by the minimum and maximum times to give the total dose/kg. If one assumes that the typical Type 1 diabetic has a weight within the range of 50 to 100 kg, and that the high and low range dose of subcutaneous prandial insulin injection is between 2 and 20 units, then the insulin/glucagon ratios can be calculated as shown in the Table below.

| Isulin/Glucagon Weight Ratios (ng/ng) and Inverse Ratio [% terms] | | | | |
|---|---|---|---|---|
| | Patient Weight | | | |
| | 50 kg | | 100 kg | |
| Infusion Duration | 150 min | 300 min | 150 min | 300 min |
| 2 U Ins/0.1 ng/kg/min Gluc | 106.6 [0.9%] | 53.3 [1.9%] | 53.3 [1.9%] | 26.7 [3.7%] |
| 20 U Ins/3.0 ng/kg/min Gluc | 39.9 [2.8%] | 17.8 [5.6%] | 17.8 [5.6%] | 8.9 [11.2%] |
| 2 U Ins/3.0 ng/kg/min Gluc | 3.59 [28.1%] | 1.78 [56.2%] | 1.78 [56.2%] | 0.89 [112.3%] |
| 20 U Ins/5.0 ng/kg/min Gluc | 21.33 [4.7%] | 10.7 [5.6%] | 10.7 [9.4%] | 5.3 [18.8%] |
| 2 U Ins/5.0 ng/kg/min Gluc | 2.133 [47%] | 1.07 [56.2%] | 1.07 [94%] | 0.53 [188%] |
| 20 U/0.1 ng/kg/min Gluc | 1067 [0.09%] | 533 [0.18%] | 533 [0.18%] | 267 [0.37%] |

Explanation of Table Entries:

For 2 U Ins/0.1 ng/kg/min Gluc: Means that a TOTAL of 2 Units of insulin are administered over the given infusion period, and that Glucagon is administered over the period of infusion at a rate of 0.1 ng/kg/min. The two number in the Table given for a 50 kg person over 150 minutes are the weight ratios of Insulin and Glucagon (absolute terms) and the weight ratios of Glucagon to Insulin in percentage terms, so: 106.6=80000 ng (2 units of Insulin)/750 ng (50×150*0.1 Glucagon); 0.9%=1/106.6 in percentage terms=inverse ratio.

In the Table above, the glucagon is present at 0.09-188% of the weight of insulin (or 0.09-112.3% when 2 U Insulin/3.0 ng/kg/min Glucagon is the upper infusion duration); for most patients, however, the glucagon will most often be administered at, or be present in a composition of the invention at <5% the weight of insulin (given that typical basal Glucagon basal replacement rates are between 0.50-0.75 ng/kg/min).

The pharmaceutical compositions for use according to the invention include all of those compositions useful in conventional methods for the control of diabetes and hypoglycemia. Such conventional methods, as that phrase is used herein, include those approved by the FDA, those in development, and those described in Diagnosis and Management of Type II Diabetes, by S. V. Edelman and R. R. Henry ($5^{th}$ Ed. PCI Publishers), the entire text of which is incorporated herein by reference, and Chapters 7 and 8 of which are especially pertinent. As used herein, a pharmaceutical formulation or pharmaceutical composition may contain a pharmaceutically acceptable excipient, diluent or carrier. By "pharmaceutically acceptable" it is meant the carrier, diluent or excipient must be compatible with the other ingredients of the formulation and not deleterious to the recipient thereof. Pharmaceutically acceptable excipients are well known in the art. See, e.g., Remington: The Science and Practice of Pharmacy (19th edition, 1995, Gennavo, ed.).

The control of diabetes by insulin therapy, as well as the control of hypoglycemia by glucagon therapy, involves parenteral administration of the insulin or glucagon. Parenteral administration may be performed by subcutaneous, intramuscular or intravenous injection by means of a syringe, optionally a pen-like syringe. The methods of the present invention can be practiced using such methodology, although, as noted above, it may be preferable in some instances to provide glucagon in a manner that ensures that its duration of action more closely matches that of the insulin employed such that the glucagon is present when the risk of hypoglycemia is greatest—typically a relatively long time after eating but still within the period in which the insulin administered continues to exert its effect.

Where subcutaneous administration of insulin and glucagon are desired, the present invention provides a variety of methods to achieve the benefits of diabetes control and prevention of hypoglycemia. In one such method, a glucagon with a shorter duration of action than the insulin is administered within about one to four hours after the insulin is administered. This method provides benefit in that most hypoglycemic episodes begin several hours after the patient has last eaten, and many patients administer insulin shortly before a meal. Thus, by delivering the glucagon a few hours after the insulin, but in any event prior to the onset of hypoglycemic symptoms, one can achieve the benefit of the invention.

In another method of the invention, the insulin and glucagon can be administered simultaneously, with the insulin and optionally the glucagon delivered parenterally, including by subcutaneous injection, but in this method, a glucagon with a longer duration of action is employed, or the glucagon is administered by a route that provides a longer duration of action. Such glucagon includes, but is not limited to, the glucagon, glucagon formulations, and routes of administration described in U.S. patent application publication No. 2002114829 and U.S. Pat. Nos. 6,197,333 and 6,348,214, which describe liposome formulations of glucagon that provide for reduced dosage effect and are long acting; PCT patent publication No. WO0243566, which describes the delivery of glucagon via trans-dermal patch; U.S. Pat. No. 5,445,832, which describes a long-acting glucagon formulation in polymeric microspheres; PCT patent publication No. WO0222154, which describes a slow-release glucagon that can have a duration of action measured in weeks; and U.S. Pat. No. 3,897,551 and Great Britain Patent No. 1,363,954, which describes the prolongation of glucagon duration by iodination. In an embodiment, the glucagon is administered as a slow-release or depot formulation (e.g., comprising polyethylene glycol).

Alternatively, parenteral administration can be performed by means of an infusion pump. A variety of insulin pumps are available and in common use that are suitable for delivery of the insulin and glucagon compositions of the invention (as well as suitable for the delivery of insulin, with glucagon being delivered by another route, such as transdermal or subcutaneous administration). Such pumps include, for example and without limitation, the pumps marketed by Medtronic (the MiniMed), Animas Corporation, Disetronic, and Dana. In this embodiment of the invention, the glucagon can optionally be administered with the insulin, and a glucagon with a short duration of action can be employed, as the glucagon can be administered as necessary. In this embodiment, the glucagon can be administered at a rate of 0.5-0.75 ng/kg/min or within the wider range of 0.10-5 ng/kg/min (alternatively, within the range 0.10-3 ng/kg/min).

Thus, in one embodiment, the present invention provides a pump suitable for the delivery of insulin, for the control of diabetes, and glucagon for the control of hypoglycemia in a human, which pump contains both insulin and glucagon. In one embodiment the pump includes a reservoir containing both insulin and glucagon. In another embodiment the pump includes insulin and glucagon in two separately controlled reservoirs. In another embodiment, the invention provides a method of controlling diabetes in a human patient with a reduced risk of hypoglycemia, said method comprising administering both insulin and glucagon to the diabetic patient using a pump of the invention.

In another method of the invention, either the insulin or the glucagon or both is provided in a formulation that is a powder or a liquid suitable for administration as a nasal or pulmonary spray or for ocular administration. A variety of such formulations are known for either insulin or glucagon, and the present invention provides methods for using these known formulations, as well as the corresponding formulations of the invention that comprise both insulin and glucagon to control diabetes with a reduced risk of inducing hypoglycemia.

Such known formulations and methods of administration useful in the methods of the invention include those in PCT patent publication Nos. WO0182874 and WO182981, which describe aerosolized insulin and glucagon; European patent publication EP1224929 and U.S. Pat. No. 6,004,574, which describe an inhaled glucagon with melezitose diluent; U.S. Pat. No. 5,942,242, which describes formulations of insulin and formulations of glucagon suitable for nasal administration; U.S. Pat. No. 5,661,130, which describes formulations suitable for ocular, nasal and nasolacrimal or inhalation routes of administration; U.S. Pat. No. 5,693,608, which describes methods and formulations for the nasal administration of insulin and for glucagon; U.S. Pat. No. 5,428,006, which describes methods and formulations for the nasal and other mucosal administration of insulin and for glucagon; U.S. Pat. No. 5,397,771, which describes methods and formulations for the mucosal administration of insulin and of glucagon; U.S. Pat. No. 5,283,236, which describes methods and formulations for the ocular administration of insulin and of glucagon; and European patent publication EP0272097, which describes a formulation of glucagon for nasal administration.

The invention also provides methods for controlling diabetes with a reduced risk of inducing hypoglycemia by administering insulin and glucagon, in which one or both of the insulin and glucagon is administered transdermally, e.g. from a patch, optionally a iontophoretic patch, or transmucosally, e.g. bucally. Manufacture and use of transdermal delivery devices is well known in the art (see, e.g., U.S. Pat. Nos. 4,943,435 and 4,839,174; and patent publication no. US 2001033858). The transdermal delivery of glucagon, and a patent publication describing transdermal formulations of glucagon, has been discussed above, and U.S. Pat. No. 5,707, 641 describes methods and formulations for the transdermal delivery of insulin.

Moreover, the methods of the invention can be practiced by oral administration of both insulin and glucagon in the therapeutically effective amounts described herein. Methods and formulations for the oral administration of insulin and of glucagon include those described in PCT patent publication No. WO9703688.

The insulin and/or glucagon employed in the methods and formulations of the invention can be supplemented with or replaced by compounds and compositions that have similar activities or effects. For example, glucagon may be replaced with glucagon mimetics. Insulin can be replaced or supplemented with insulin secretagogues including, but not limited to, sulfonylureas such as Acetohexamide (DYMELOR), Chlorpropamide (DIABINESE), Tolazamide (TOLINASE), Tolbutamide (ORINASE), Glimepiride (AMARYL), Glipizide (GLUCOTROL), Glipizide Extended Release (GLUCOTROL XL), Glyburide (DIABETA, MICRONASE), Glyburide Micronized (GLYNASE, PRESTAB); Meglitinides such as Nateglinide (STARLIX) and Repaglinide (PRANDIN); Gastric Inhibitory Polypeptide (GIP) [Stimulates GLP-1 ouput]; Glucagon-like peptide (GLP)-1; Morphilinoguanide BTS 67582; Phosphodiesterase inhibitors; and succinate ester derivatives; insulin receptor activators; insulin sensitizing. Biguanides such as Metformin (GLUCOPHAGE), Thiazolidinediones (TZD) such as Troglitazone (REZULIN), Pioglitazone (ACTOS), and Roziglitazone (AVANDIA); Non-TZD peroxisome proliferator activated receptor γ (PPARγ) agonist GL262570; Alpha -glucosidase inhibitors such as Acarbose (PRECOSE) and Miglitol (GLYSET); Combination agents such as Glucovance (GLUCOPHAGE with GLYBURIDE); Tyrosine Phosphatase Inhibitors such as Vanadium, PTP-1B inhibitors, and AMPK activators, including 5-aminoimidazole-4-carboxamide ribonucleoside (AICAR); and other agents such as Exendin (EXENATIDE (synthetic exendin-4)) and Amylin (SYMLIN® (pramlintide acetate)). In one embodiment the only pharmaceutically active components of the formulation of the invention are insulin and glucagon. In one embodiment, the pharmaceutical composition (e.g., containing both insulin and glucagon) is not formulated as an aerosol and/or does not contain troglitazone hydrochloride (and may not contain any thiazolidinedione). In an embodiment, the formulation is not administered orally and/or is not administered nasally.

The methods and compositions of the invention may be used to treat human patients as well as other mammals (e.g., rats, mice, pigs, non-human primates, and others). In some embodiments the human patient is a child or juvenile; in one embodiment the human patient is an adult. In some embodiments the patient is a type I diabetic. In one embodiment the patient is a type II diabetic. In one embodiment the patient is a brittle type I or type II diabetic. In one embodiment, the non-human mammal is a animal models for the study of diabetes, e.g., Zucker diabetic-fatty (ZDF) rats, and db/db mice.

The following examples describe illustrative embodiments of the invention.

EXAMPLE 1

Co-administration of Glucagon Parenterally and Insulin for the Control of Diabetes and Prevention of Hypoglycemia The glucagon currently available in the North American market is human glucagon of rDNA origin produced by Eli Lilly & Co or Bedford Labs (Novo). Four brand names are known, these being: Glucagon Diagnostic Kit (Lilly); Glucagon Emergency Kit (Lilly); Glucagon Emergency Kit for Low Blood Sugar (Lilly); and GLUCAGEN (Bedford Labs).

Novo produces glucagon under its own name outside of North America. Novo produces its glucagon in yeast and Lilly produces its glucagon in *E. coli*. The following examples illustrate practice of the methods of the present invention using such commercially available glucagons and insulins administered via a variety of routes.

The Lilly glucagon is typically provided in kit form. The glucagon within the kit is in the form of a powder within a sterile vial with a standard rubber-sealed neck. The vial contains a mixture of 1 mg of lyophilized glucagon, 49 mg lactose, and hydrochloric acid to adjust the pH (glucagon is soluble below pH 3 or above pH 9.5). The patient injects 1 ml of diluent from a pre-filled syringe (which contains 12 mg/ml of glycerine in a mixture of water, and hydrochloric acid) into the vial. The vial is shaken until the solution is clear. The liquid is returned to the syringe, and the entire dose is injected (children are typically administered 50% of the standard dose.).

Glucagon is administered parenterally by subcutaneous, intramuscular, and intravenous routes, with the pharmacokinetic properties differing accordingly as understood by those of skill in the art. Maximum plasma concentration is achieved approximately 20 minutes after subcutaneous administration. The half life in vivo ranges from 8 to 18 minutes. Peak plasma concentration of approximately 8 ng/ml are achieved after approximately 20 minutes, and elevated glucose levels persist for approximately 1½ hours after administration and begin rising almost immediately following administration. Patients with insulin-induced coma will typically recover consciousness within 15 minutes of glucagon administration. Parenteral glucagon, when given to treat hypoglycemia, does so primarily by increasing serum glucose availability through increased output of glucose by the liver (the conversion of glycogen to glucose and formation of new glucose by gluconeogenesis).

There are a wide variety of insulin dosage regimes in use. The regime used depends on whether type-1 or type-2 diabetes is being treated and on a large number of factors specific to the individual being treated. It is normal medical practice to replace insulin using a combination of parenterally administered insulins (usually subcutaneously) of rapid onset/short acting duration (LISPRO (HUMALOG) or ASPART (NOVOLOG)), slower onset/short acting duration (regular human insulin), intermediate duration (NPH or LENTE), long acting duration (ULTRALENTE) and 24 hour peak-less duration (GLARGINE (LANTUS) and DETEMIR).

The dosage regimes can be quite complex. For example, a typical twice-daily regimen might involve administering short acting and intermediate duration insulin before breakfast and supper. The insulin profile thus obtained has a number of peaks, which roughly correspond to the anticipated post-prandial glucose output, as well as providing a basal insulin level throughout any 24 hour period. This is illustrated in FIG. 1 [taken from http://www.uptodate.com/patient_info/topicpages/pictures/ins_time.gif], which shows the idealized pharmacokinetics for a mixture of regular and intermediate acting insulin. Insulin levels can vary significantly between individuals and even within the same individual, depending on factors such as site and depth of injection, local blood flow, total volume and type of insulin injection, and other factors appreciated by those of skill in the art. Thus, there can be significant inter and intra-patient variability in subcutaneous absorption of insulin, which increases the likelihood of variations in serum glucose, including the possibility of hypoglycemia.

With the advent of the rapid onset insulins and a long acting insulin with little or no peak appearance (GLARGINE (LANTUS); also, DETEMIR is a long acting insulin in development; in addition, ULTRALENTE is a long acting insulin but tends to have some peak effect in most patients), it became possible to manage insulin levels (and hence blood glucose levels) with more accuracy. The basic methodology is to replace basal insulin and prandial insulin through the combined use of insulin preparations having different rates of onset and durations of action. This may involve the use of separately administered insulins of differing onset, (e.g. GLARGINE and LISPRO) or the use of various pre-mixed formulations, (e.g. 70/30-70% NPH and 30% regular combined), which are commercially available for this purpose.

The point at which the glucagon is administered in accordance with the methods of the invention is before, during, or immediately prior to the period when insulin action is most unopposed, for example when significant insulin action persists in the absence of sufficient serum glucose availability. Thus, insulin-induced hypoglycemia may occur whenever there is a mismatch between circulating insulin and glucose levels (a relative excess of insulin effect to glucose availability).

A. Insulin Administered Parenterally (i) GLARGINE/LISPRO Insulins

For this illustrative example, the patient (all patients referred to herein are fictitious; any resemblance to an actual person is coincidental) is an adult male, 50 years of age, weighing 75 kg, with 5 L of blood, suffering from type-2 diabetes and using insulin therapy (without concomitant oral combination therapy). He has been using insulin for over 10 years and his glucagon response to hypoglycemia is minimal. His insulin regimen involves basal insulin replacement using GLARGINE (LANTUS) subcutaneous injections at a dosage level of 20 units administered at bedtime in addition to prandial insulin injections of LISPRO (HUMALOG) of between 5 and 10 units (depending on the amount of carbohydrate consumed) administered at mealtimes.

Figure 2:
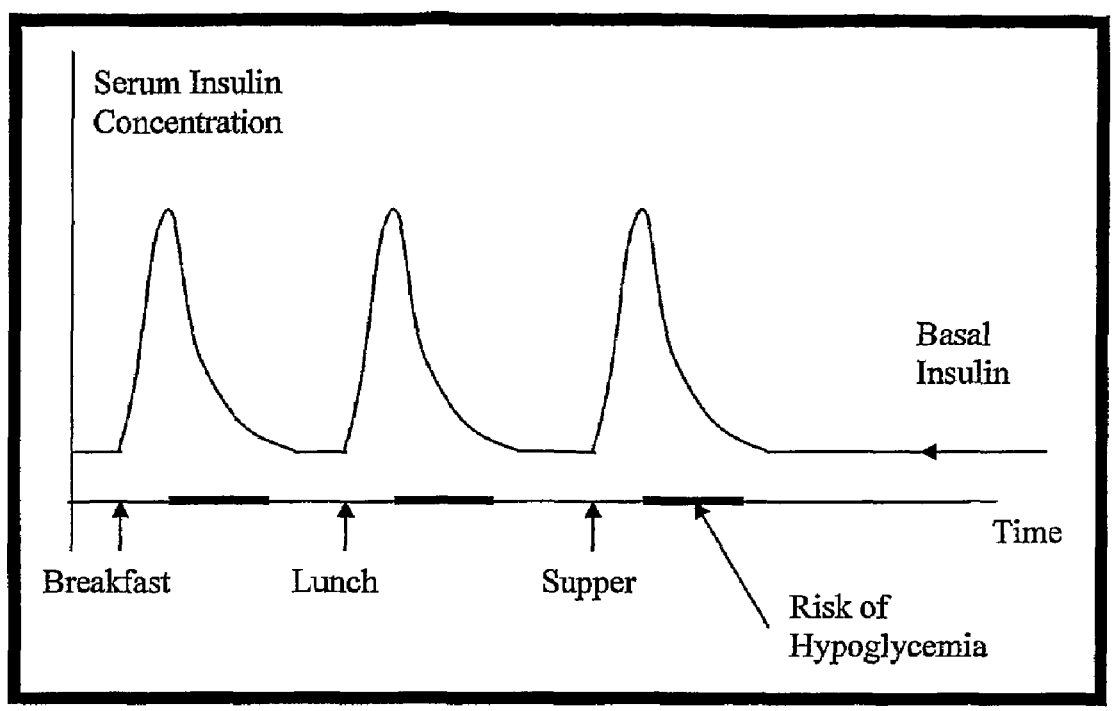
FIG. 2 is a graph illustrating the insulin profile of a hypothetical patient, as described in Example 1, Part A(i), showing a very simple, flat line graph (basal level set by the GLARGINE (LANTUS)) punctuated by peaks corresponding to prandial LISPRO (HUMALOG) insulin injections.

His insulin profile is very simple, being a flat line (basal level set by the GLARGINE (LANTUS)) punctuated by peaks corresponding to the prandial LISPRO (HUMALOG) insulin injections. This insulin profile is shown in FIG. 2. In this patient, the risk of hypoglycemia typically arises between 2 and 5 hours after the meal. It is during this period that administering glucagon is most efficacious and effective in preventing the possibility of a hypoglycemic episode. In non-diabetics, glucagon usually falls following a carbohydrate meal (in response to increased glucose levels) and then recovers subsequently as glucose levels return to normal. In type-1 diabetics (and type-2 diabetics of 5 years or more) the glucagon response to low serum glucose is limited. Hence, if insulin causes the serum glucose level to drop well below the basal level, hypoglycemia will ensue.

Hypoglycemic symptoms are typically observed in diabetics at glucose levels less than 50 mg/dl, or sometimes less than 40 mg/dl. In normal individuals, glucagon release would be augmented (by about 40 pg/ml or higher, e.g. about 60 pg/ml or higher) before glucose levels fell this low and would prevent the onset of hypoglycemic symptoms. However, glucagon production to hypoglycemic is deficient in most 0.10 to insulin-treated diabetics. Thus, administering glucagon to achieve these levels during the period of susceptibility will prevent or attenuate the severity of hypoglycemic attack.

A unit of glucagon administered to a patient will produce a peak concentration of approximately 8 ng/ml (see Lilly's "Information for Physicians" sheet). Hence the dose required to provide prophylaxis can be estimated to be about ½₀₀th of a unit (lasting from between 1 and 3 hours in its effect). This dose corresponds to between 1.25% and 2.50% by weight of the insulin used (5-10 IU of insulin).

Thus, in accordance with the methods of the invention, this patient is administered ½₀₀th of a unit of glucagon (using Eli Lilly's Glucagon Emergency Kit as described above administered subcutaneously) two hours after the meal. Two similar doses are administered hourly for an additional two hours. This makes three doses at hours 2, 3 and 4, providing protection from hypoglycemia for 3 hours beginning 2 hours after the meal. This dosage level (summing over the three doses of glucagon) corresponds to between 3.75% and 7.50% by weight of the prandial insulin administered (5-10 IU insulin). In practice of the invention with formulations comprising both insulin and glucagon, one can use the lower percentage of glucagon (3.75%), as the risk and degree of hypoglycemia is (in part) insulin-dose-dependent. In this example, while the glucagon concentration from the dose administered 2 hours after the meal will have fallen back to approximately basal levels after an hour, the elevation of blood sugar due to this dose will persist for more than one hour, giving time for the second dose to take effect. The same pharmacokinetics applies to the third dose of glucagon. In an alternative embodiment, two doses or even one dose of glucagon can be administered.

Although this example employs a simple basal and prandial insulin model, it will be understood by those skilled in the art to be applicable to all currently practiced dosage regimens. The timing (and frequency) of the glucagon injections may be adjusted to match the period in which the patient is most susceptible to hypoglycemia, i.e. the point at which insulin action and glucose availability are most mismatched.

(ii) NPH/Human Insulins

A typical diabetic patient is an adult male, 63 years of age, weighing 75 kg, suffering from type-2 diabetes for 18 years and using combination insulin therapy (without concomitant oral anti-diabetic therapy). In the past, he will typically have used oral anti-diabetic medications, including Glyburide and Glipizide, but these will have been stopped and insulin started when his serum glucose levels were consistently above 250 mg/dl. He will have been using insulin of one type or another for over 10 years and will have developed evidence of background retinopathy, mild renal impairment with a serum creatinine of 1.9 mg/dl and creatinine clearance of 60 ml/min, mild proteinuria, bilateral distal symmetrical neuropathy in both feet, and exertional angina. His insulin regimen would typically involve a split-mixed regimen of subcutaneous NPH insulin, 20 units before breakfast and 15 units before dinner, which is intended to provide day-long basal insulin coverage plus modest postprandial coverage for lunch and the evening meal (and bedtime snack). In addition, he injects regular insulin of between 6 and 10 units (depending on the level of pre-meal serum glucose as well as the size and carbohydrate content of the meal) before these meals.

His insulin profile is similar to that shown in FIG. 1, with less rapid peaks and slower decays resulting from the prandial injections of regular insulin and slower onset and delayed decay effects from the twice daily intermediate acting NPH insulin. His fasting glucose levels are typically well controlled in the range of 90-130 mg/dl, but his 1-2 hour postprandial glucose levels are suboptimal and generally range from 180 240 mg/dl. Glycosylated hemoglobin is elevated at 7.9% (normal range 4-6%). Efforts to increase his breakfast or evening meal dose of prandial regular insulin to reduce postprandial glucose levels is usually accompanied by frequent intermittent hypoglycemia, of mild to moderate severity, often 1-2 hours before lunch or dinner. These episodes of hypoglycemia can be quite severe and associated with symptoms of sweating, tremors, nausea, and headaches, particularly when he is late for meals. He has never had insulin-induced hypoglycemic coma but is reluctant to increase his insulin dosage in case this happens. He fears that he could lose his driver's license if this occurs or perhaps his job as a night watchman. Because of this patient's long history of diabetes and presence of significant complications, it is expected that he will exhibit impaired glucose counter-regulation to hypoglycemia, especially manifest as a blunted or absent glucagon response.

In this patient, the risk of hypoglycemia is usually greatest between 3 and 5 hours after a meal (late postprandial hypoglycemia), when circulating insulin levels are still increased above fasting level but glucose availability (from gastrointestinal absorption and liver production) is minimal. It is during this period, prior to the onset of hypoglycemia, that the administration of glucagon would be most efficacious and effective in preventing the possibility of hypoglycemic episodes by increasing circulating glucose availability. In non-diabetic individuals, both insulin and glucagon are tightly regulated following a meal to balance glucose production and utilization so as to maintain normoglycemia. Should insulin effects become pronounced, glucagon levels will rise to offset this hypoglycemic potential.

To prevent the development of hypoglycemia in accordance with the methods of the invention, this patient is administered 1/50th of a unit (20 μg) of glucagon given subcutaneously (optionally using Eli Lilly's Glucagon Emergency Kit, as described above) two to three hours after each meal. In one embodiment, the glucagon is added when glucose measurements indicate glucose levels are approaching hypoglycemic levels. This administration provides the required protection between hours 3 and 5, as described above. Because one unit of glucagon (1 mg) will produce a peak concentration of approximately 8 ng/ml, 1/50th of a unit will produce a peak concentration of approximately 160 pg/ml, which is intended to approximate normal basal levels and ensure that unopposed insulin action does not occur. This dosage level corresponds to less than 3% by weight of the prandial insulin administered.

Although this illustrative example employs a simple basal and prandial insulin model, it will be understood by those skilled in the art to be applicable to virtually all currently practiced insulin dosage regimens. The glucagon injections are optimally timed and vary depending on the insulin regimen used but are designed to achieve sustained glucagon levels during the expected periods of relatively unopposed insulin action.

In the current hypothetical example, this situation tends to occur at several times-throughout the day. For example, hypoglycemia is prone to occur when the "tail" of injected regular insulin absorption combines with peaking insulin availability from the intermediate acting NPH. This situation occurs several hours after breakfast when serum glucose availability (primarily from gut absorption and liver production) is minimal or decreasing. Similar situations also often occur before dinner, at bedtime, and in the middle of the night. Thus, for all insulin dosage regimens, the timing of glucagon injection in accordance with the methods of the invention can vary depending upon the pharmacologic characteristics and timing of the insulin(s) used.

To offset the glucose-raising potential of the administered glucagon, the dose of insulin acting during that hypoglycemic period can be increased somewhat to maintain euglycemia. However, the increased availability of glucagon provides a buffering action or cushion to the excessive glucose lowering action of insulin in those specific circumstances as described above and blunts or prevents hypoglycemia.

B. Insulin Administered by Pump

In this example, the patient described in Example 1.A.i uses a pump to administer his insulin requirement. Example 2, below, describes the administration of insulin by pump. Instead of administering basal insulin by GLARGINE (LANTUS) once daily as in Example 1.A.i, the patient's insulin pump is programmed to provide a continuous stream of rapid-onset insulin (e.g. LISPRO or ASPART). In this example, he administers ASPART in doses of between 5 and 10 units at mealtimes according to the pre-meal glucose level and the amount of carbohydrate and calories consumed. The patient will then in accordance with the methods of the invention administer 1/200th of a unit of glucagon (using Bedford Lab's GLUCAGEN product, for example) two hours after the meal and repeat the dose hourly for another two hours. The glucagon is administered subcutaneously. This administration provides protection from hypoglycemia between hours 2 and 5, as described in Example 1.A.i.

C. Insulin Administered Transdermally [Including Patch and Topical Cream]

In this example, the patient is a 62 year old lean type-2 diabetic of 6 years duration. He was initially treated with Glyburide 20 mg twice daily and subsequently with the addition of Metformin 1 gram twice daily, but fasting and postprandial blood sugars were consistently in the range of 200-350 mg/dl. He is advised by his physician that insulin is required. The oral anti-diabetic medications are discontinued and GLARGINE (LANTUS) insulin 15 units is administered at bedtime to provide his day-long basal insulin replacement needs. Postprandial insulin is administered by transdermal patch to provide 2-6 units of rapidly acting insulin (patches available in 2 unit increments; although this example refers to use of a patch, those of skill in the art will appreciate that substantially similar methodology is employed to practice the invention with insulin or glucagon delivered transdermally by other means, such as creams or lotions). Alternately, he is offered the 24-hour basal insulin replacement patch instead of once daily GLARGINE. The basal insulin replacement patch contains insulin in a unique formulation designed to provide steady continuous absorption and low constant serum insulin levels throughout the day. Because of persistent elevation of fasting plasma glucose, his physician progressively increases his dose of GLARGINE insulin over 6 months to 24 units and transdermal patches to 4-10 units. With this increase in GLARGINE and transdermal insulin dosage, fasting glucose levels ranged from 70-110 mg/dl and 1-2 hour postprandial glucose levels from 130-180 mg/dl within 3 months.

The patient applies the rapidly-acting insulin patches 30-60 minutes prior to meals. This timing is chosen so that absorption of the meal coincides with insulin patch absorption kinetics and action. This patient has near normal glycemic control as indicated above but begins to suffer from early morning hypoglycemia, typically at 1 or 2 a.m. At these times, this hypothetical patient is frequently confused, irritable, and at times anxious. Several readings of fingerstick glucose taken during these events reveal blood glucose values of 35-40 mg/dl with prompt resolution of symptoms with ingestion of juice. In an effort to control these bouts of hyperglycemia, his physician gradually decreases the evening dose of GLARGINE, but this is associated with deterioration in glycemic control and, primarily, elevation of pre-prandial glucose levels.

To restore near-normal glycemia but prevent early morning hypoglycemic symptoms in accordance with the methods of the invention, the physician increases the GLARGINE insulin back to 24 units at bedtime and prescribes administration of subcutaneous glucagon 1/200th of a unit (using Bedford Labs Glucagon product) immediately following the injection of GLARGINE at ~23:00. The time of administration of glucagon depends primarily on the rate of absorption, which is rapid, reaching peak levels within 15-30 minutes, and a duration of action of approximately 2-3 hours. The aim is to provide a level of plasma glucagon approximating normal basal levels during this period and prevent an unopposed action of insulin from GLARGINE insulin or a delayed action of the early evening (pre-dinner) patch. This therapy provides the required protection from hypoglycemia for approximately 3 hours after the GLARGINE injection, as described above. With the addition of bedtime glucagon to his diabetes regimen, the early morning hypoglycemic episodes should resolve and day-long near-normal glycemia be preserved.

D. Insulin by Inhalation [Including Pulmonary, Buccal, Nasal and Sublingual]

This example is similar to Example 1.A.i, except the patient administers insulin by inhalation rather than by subcutaneous injection. Example 4, below, describes the administration of insulin by inhalation. It will be understood by those skilled in the art that similar methods apply when insulin is administered buccally, nasally, or sublingually in accordance with the methods of the present invention. The patient will either continue to administer his basal need via GLARGINE (LANTUS) or he will utilize an insulin inhaler to administer basal insulin needs. The patient will administer his prandial insulin need (equivalent to between 5 and 10 units administered by subcutaneous administration) using his insulin inhaler (either pulmonary, nasally, buccaly or sublingually).

In accordance with the methods of the invention, the patient will then administer 1/200th of a unit of glucagon (optionally using Lilly's Glucagon kit) two hours after the meal and another two doses hourly thereafter. He will administer the glucagon subcutaneously. This will provide the required protection from hypoglycemia between hours 2 and 5, as described in Example 1.A.i.

EXAMPLE 2

Co-administration of Glucagon by Pump and Insulin for the Control of Diabetes and Prevention of Hypoglycemia Insulin can be administered by pump in accordance with the methods of the present invention. There are a number of pumps commercially available (or soon to be available) in the US market and elsewhere that are suitable for use in the present methods. These include but are not limited to:

ANIMAS (IR-1000)

DELTEC (Cozmo pump)

DISETRONIC (H-TRONplus and D-TRONplus)

LIFESCAN & DEBIOTECH (MEMS Insulin Pump in development)

MEDTRONIC MINIMED (PARADIGM Insulin Pump and 508 Insulin Pump)

MEDTRONIC MINIMED (2007 Implantable Insulin Pump System (EU only))

When both the insulin and the glucagon are to be administered by pump (from separate reservoirs), a number of configurations can be employed in the practice of the present invention. Typical configurations are:

(1) A single device with a single pump and two reservoirs (for dual reservoir pumps, see, for example, U.S. Pat. No. 5,474,552) with each drug delivered through 2 separate lines that are merged prior to cannulization;

(2) A single device with a single pump and two reservoirs with each drug delivered through 2 separate lines, each of which is independently cannulized;

(3) A single device with two independent pumps and two reservoirs with each drug delivered through 2 lines that are merged prior to cannulization;

(4) A single device with two independent pumps and two reservoirs with each drug delivered through 2 separate lines, each of which is independently cannulized;

(5) Two devices, each with a single pump and one reservoir, with each drug delivered through 2 separate lines that are merged prior to cannulization; and (6) Two devices, each with a single pump and one reservoir, with each drug delivered through 2 separate lines independently cannulized.

It will be understood by those skilled in the art that other configurations are possible and that the practice of the invention is not limited to the devices and device configurations listed above. For example, implantable pumps may be used to practice the invention in almost exactly the same way as is achieved using external pumps.

Embodiment (1) above minimizes trauma to the patient on cannulization, reduces cost, simplifies infusions, and minimizes complexity. With this embodiment, the single pump can be programmed to deliver appropriate volumes from each reservoir, each containing different concentrations of one of the two hormones. Such a pump is provided by the present invention.

In a typical insulin pump, the internal pump mechanism usually comprises an electromagnetically driven pulsatile pump having a solenoid operated piston mounted for reciprocation within a cylinder to draw medication from an internal storage chamber (reservoir), and to deliver such medication through the delivery line and then via a cannula or micro-cannula to the patient.

Because delivery lines used with pump insulin are typically one-half to one meter in length with lumen diameters of the order of $1/10$th of a millimeter (dead volume of the order of a $1/10$th of a milliliter or about 10 IU of Insulin), the time delay between a new drug reaching the body and the time at which the pump starts infusing it is likely to be substantial (about half a day).

To reduce this delay, the present invention provides pumps with lines of much shorter length and/or of very small internal lumen diameter that enable the lag time between a switch in drugs to be much shorter. The present invention also provides peristaltic type pumps acting on two delivery lines.

The present invention also provides a system comprising a pump and a set of four valves, two immediately before and two immediately after the pump, which when operated in pairs, control which drug is pumped. The two lines are, in one embodiment, merged at the point of cannulization, thereby eliminating the lag or (dead volume) time. The extra space required for the electronically actuated micro-valves is minimal and adds little bulk or expense and can be assembled using commercially available devices. Additional possibilities involving the use of fewer than 4 valves are described below.

An economical pump system suitable for use in the methods of the invention is a micro-pump known as MEMS (Micro-Electro-Mechanical System), being developed for diabetes by Debiotech under the brand name Chronojet. The use of two such micro-pumps in a unitary device adds little bulk and only minimal expense to existing designs. As noted above, the two delivery lines can be merged (in the sense that the two drugs come into direct contact) at the point at which they connect to the cannula or similar micro-needle device used to puncture the skin and deliver the drug.

In one embodiment, a single split-lumen (dual lumen) line is used instead of two physically separate lines. This method has the advantage that the patient has only to route one flexible delivery line rather than two. Alternatively, two standard lines physically adhered along their lengths can be used in accordance with the methods of the invention to achieve the same advantage.

Figure 3:
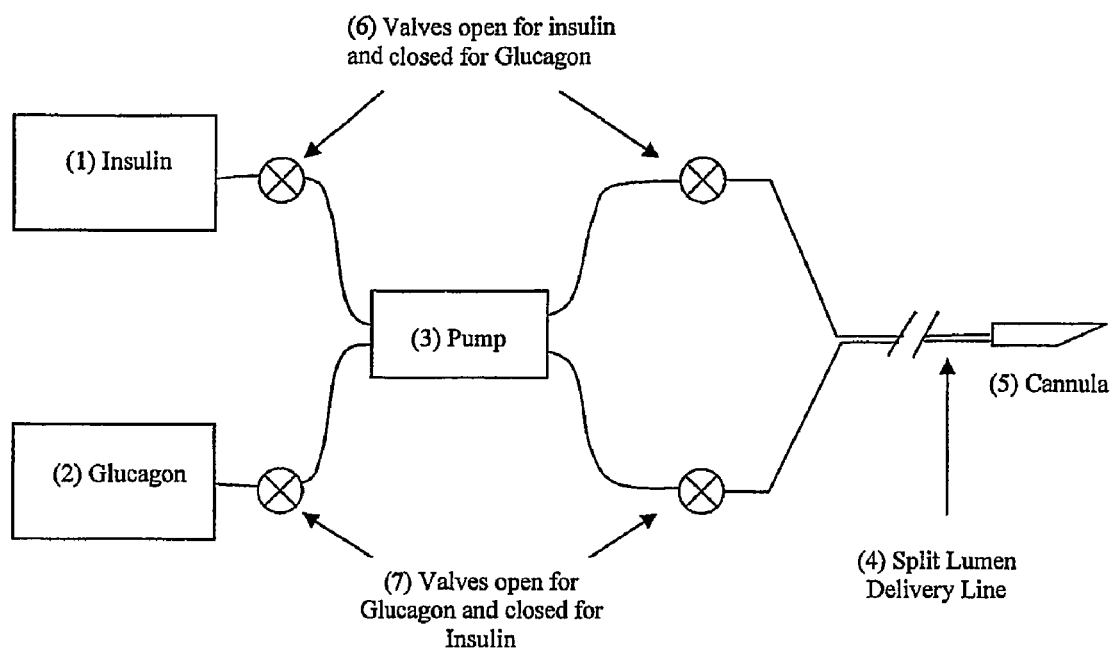
FIG. 3 is a schematic of a drug delivery pump configured for practice of the present invention.
Figure 4:
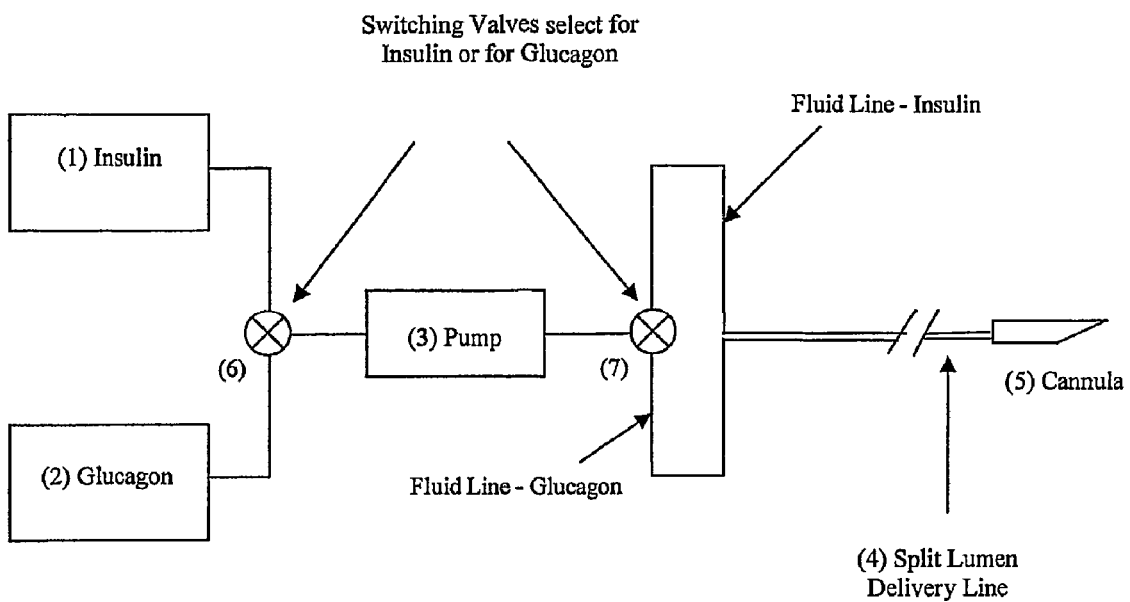
FIG. 4 is a schematic of a drug delivery pump configured for practice of the present invention.
Figure 5:
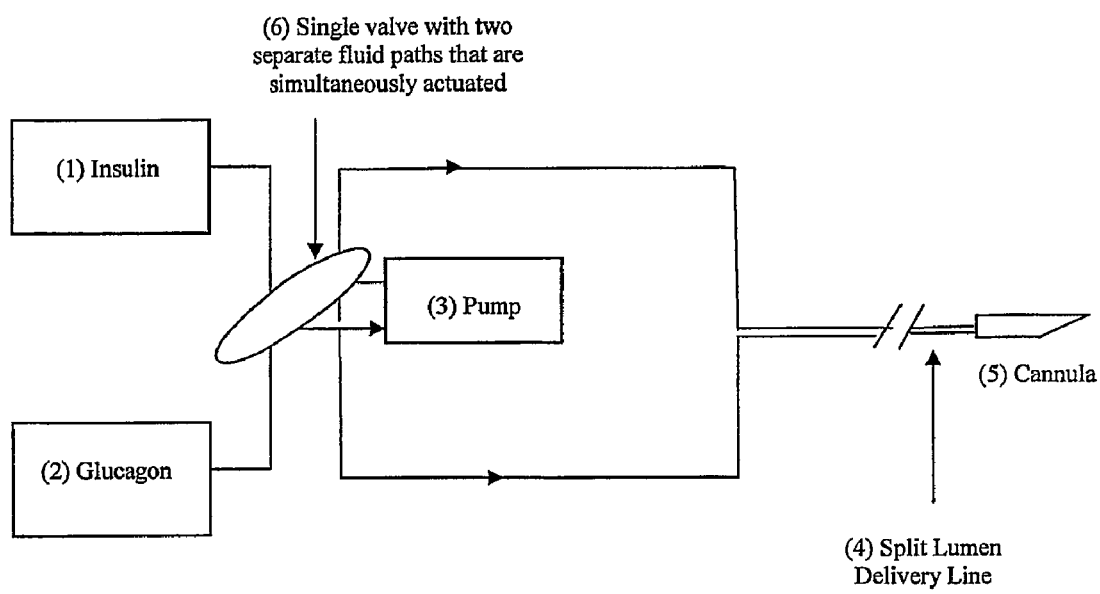
FIG. 5 is a schematic of a drug delivery pump configured for practice of the present invention.

In one embodiment, therefore, the pump of the invention is a currently used insulin pump modified to have two drug reservoirs instead of one, each being independently administered by a single (or dual) pump and a single control system to manage the quantity and relative timing of administration of the two drugs. As noted above, the device can in some embodiments comprise 1, 2 or 4 valves and appropriate connective tubing. Schematics of devices that can be used in accordance with the methods of the present invention are shown in FIGS. 3, 4, and 5. In FIG. 3, the insulin reservoir (1) and the glucagon reservoir (2) have lines in fluid communication with pump (3) and then on to the cannula (5) via split lumen delivery line (4) by way of 4 valves (6) and (7). When valves (6) are open and valves (7) are closed, only insulin is pumped. When valves (6) are closed and valves (7) are open, only glucagon is pumped. In this way, a single pump may be used to deliver insulin or glucagon to the patient, either simultaneously or separately, with minimal mixing of the two substances by virtue of delivery through a split lumen delivery line in which the liquids only mix at the cannula, i.e. the point of deliver. In FIG. 4, the insulin reservoir (1) and the glucagon reservoir (2) have lines in fluid communication with pump (3) and then on to the cannula (5) via split lumen delivery line (4) by way of 2 valves (6) and (7). These are 2-way valves that allow either the insulin path or the glucagon path to be open—but only one at a time. A small amount of mixing of the two fluids will take place in the small stretch of line through the pump, but this will be an insignificant volume when compared to typical pumping volumes. In this way, glucagon and insulin may be delivered to the patient with minimal mixing and dead space in the lines. The advantage of this construction over the construction described disclosed by FIG. 3 is that only two valves are required for operation. In FIG. 5, the configuration here is the same as that disclosed in FIG. 4, but in this case the two valves (6) and (7) are combined into a single device with a unitary actuation mechanism. In this way the mechanism is kept as cheap and simple as possible, with only one valve and one pump required to achieve the desired result.

It is normal practice with pumped insulin for the patient to set the pump to deliver a basal level of insulin and to intervene manually to administer prandial insulin as required.

In one embodiment, the glucagon delivery is automatically administered over the appropriate period (for example continuously between the 3rd and 5th hours following the manual instruction to deliver the prandial insulin). The control logic required to produce such a sequence of events can be programmed into the pump.

A. Insulin Administered by Pump

This example illustrates how the methods of the present invention can be practiced using pump-based administration. A typical hypothetical patient is an adult male, 35 years of age, weighing 75 kg, having type-1 diabetes since the age of 15 and using insulin therapy from the time of diagnosis. He has been on a number of different insulin regimens previously with less than optimal glycemic control. In the last 5 years, he has begun to develop significant background retinopathy, mild renal insufficiency, and hypertension, and is concerned that these complications will continue to progress rapidly unless he is able to improve glycemic control from his current glycosylated hemoglobin level of 7.8%. Most recently, he has been on ULTRALENTE 22 units at bedtime and LISPRO insulin 4-8 units just prior to each meal and snack. The dose of ULTRALENTE has been adjusted to provide basal replacement of insulin, while the dose of prandial LISPRO varies depending upon the prevailing pre-injection serum glucose and total calories and carbohydrate content of each meal.

Despite self-monitoring of capillary blood glucose by glucometer 46 times per day, his glycemic control is often erratic, ranging from high values in the 200 mg/dl range to occasional hypoglycemia. In the previous year, he has had 3 bouts of severe hypoglycemia with coma or near coma, two occurring while at work and the other following a game of handball. All required the assistance of others and in the post-exercise case required the intramuscular injection of glucagon by paramedics. He married 16 months ago and is committed to do whatever is necessary to achieve improved glycemic control. He has decided with his physician that a programmable insulin infusion pump offers him the best opportunity to achieve this goal, and he began using this device nearly one year ago.

With using insulin pump therapy, short acting insulin is typically used, because the pump provides a continuous feed to simulate basal insulin over the long term. In this example, the patient uses ASPART (NOVOLOG) as his insulin of choice. The pump, reservoir, and control mechanism (in this illustrative case, the MEDTRONIC MINIMED PARADIGM INSULIN PUMP) can be attached at various sites about the body of the patient (most commonly on the belt, for example), and is linked by a flexible plastic tube to the micro-cannula he has inserted in his abdomen, thigh, or arm (women tend to place the infusion site in the lower abdomen while men usually choose the upper abdomen).

The patient has programmed the device to deliver 1 IU of insulin every 50 minutes (20 units a day). When the patient eats during the day, he programs the device to release an amount of insulin (between 3 and 8 units) appropriate to his meal situation pre-meal glucose, total calories, and carbohydrate content). He does this by pushing the appropriate buttons on the device (or by use of a remote control device, if available) to select the size of the insulin bolus required.

Following use of the programmable insulin infusion pump, the patient has been able to achieve a marked improvement of glycemic control, with pre-prandial glucose levels ranging from 70-110 mg/dl, postprandial (1-2 hour) levels of 120-160 mg/dl, and glycosylated hemoglobin of 6.4%. However, he continues to be plagued by frequent mild-to-moderate hypoglycemic episodes that he frequently doesn't recognize until he measures his fingerstick glucose. Many of these low glucose values are in the range of 30-40 mg/dl. He has been told by his wife and friends that at times he behaves inappropriately but improves with ingestion of food or juice.

Because of the long duration of type-1 diabetes and frequent and often unrecognized hypoglycemia, this patient has significant impairment of glucose counter-regulation with absent glucagon and markedly blunted epinephrine response to hypoglycemia. That is, he is unable to mount an effective response to abnormally low blood sugar and the attendant dangers that can result. Furthermore, he has hypoglycemic unawareness, which frequently accompanies recurrent hypoglycemia and increases the risk of severe hypoglycemia developing. He is unaware when his blood sugar is dangerously low, because his body's mechanisms to recognize low blood sugar are defective. This is a common scenario in diabetes of long duration and manifests itself most commonly when efforts to achieve normal or near-normal glycemic control are attempted in such individuals. Because of his concern about the increasing frequency and severity of his hypoglycemic episodes and his frequent inability to recognize them, he is seriously considering "loosening up" his glycemic control to reduce the hypoglycemia. He understands that this may have detrimental consequences with increased microvascular complications but feels that the dangers of severe hypoglycemia are greater and more immediate.

This hypothetical patient has been striving to achieve the best glycemic control possible based on the understanding that the risk of developing microvascular complications is minimised so long as his day-long glycemia approaches non-diabetic levels. Despite being on the most advanced and flexible form of insulin delivery system currently available and having achieved significant improvement in glycemic control to recommended goals, he is plagued by frequent and potentially dangerous bouts of hypoglycemia. To alleviate this situation, yet allow him to maintain the same level of glycemic control, the methods of the present invention are used, and in one embodiment, a second pump device, which can be identical to the first but has a glucagon cartridge in place of the insulin cartridge, is employed. The device is independently cannulized and independently controlled for continuous subcutaneous infusion of glucagon when desired.

The patient is instructed to practice the invention as follows. After taking a meal, the patient administers his prandial insulin (3-8 units) and at the same time programs his glucagon pump to administer $\frac{1}{50}$th of a unit (20 µg) of glucagon over three hours and timed to begin 2-3 hours after administration of his prandial insulin. In this example, unlike in Example 1.A.ii, the continuous release of glucagon produces a smoother profile with less of a peaked appearance and decay period than with a single subcutaneous injection of glucagon. The increased availability of glucagon during this patient's period of greatest susceptibility to hypoglycemia substantially decreases both the likelihood and severity of such events. To offset the glucose-raising potential of subcutaneous administered glucagon, the dosage of infused insulin can be increased to maintain euglycemia during the period of glucagon administration. By administering glucagon in this way, the patient is provided with sufficient glucagon to serve as a cushion or buffer to the unopposed action of insulin so as to prevent the risk of a hypoglycemic episode. Thus, the administration of glucagon enables the patient to maintain good glycemic control without the excessive risk of frequent and severe hypoglycemia.

B. Insulin Administered Parenterally

The invention may be practiced by administering glucagon by pump and administering insulin parenterally, including by pump or other subcutaneous administration. Pumps suitable for insulin administration are also suitable for glucagon administration and are discussed in Example 2. Insulin can be administered parenterally as described in Example 1.A.i. Instead of injecting glucagon as described in Example 1.A.i, however, the pump is programmed (or actuated) to deliver glucagon continuously between hours 2 and 5 after the meal. The total dose of glucagon released is approximately $\frac{3}{200}$ths of a unit over those three hours, this being sufficient to provide protection from hypoglycemia.

C. Insulin Administered Transdermally [Including Patch and Topical Cream]

Insulin may be administered transdermally in the practice of the invention. In accordance with Example 1.C, the patient administers his insulin needs by use of transdermal patch (or cream). Instead of administering the glucagon parenterally as described in that example, however, the patient uses an insulin pump (containing not insulin but glucagon) to administer glucagon to prevent hypoglycemia in the early morning. Before going to bed, the patient programs his pump to deliver ½₀₀th of a unit of glucagon between the hours of 01:00 and 02:00, the period during which he is most susceptible to hypoglycemia. By so doing, the patient is able to maintain euglycemia using the methods of the present invention without the risk of hypoglycemia occurring during his sleep.

D. Insulin Administered by Inhalation [Including Pulmonary, Buccal, Nasal and Sublingual]

In accordance with Example 1.A.i, the patient administers insulin by inhalation rather than by subcutaneous injection. Example 4 describes the administration of insulin by inhalation. It will be understood by those skilled in the art that similar methods can be employed when insulin is administered buccally, nasally or sublingually. The patient will either continue to administer his basal need via GLARGINE (LANTUS), or he will utilize an insulin inhaler to administer basal insulin needs. The patient will administer his prandial insulin need (equivalent to between 5 and 10 units administered by subcutaneous administration) using his insulin inhaler (either pulmonary, nasally, buccaly or sublingually). Instead of injecting glucagon as described in Example 1.A.i, however, an insulin pump (containing glucagon rather than insulin) is programmed (or actuated) to deliver glucagon continuously between hours 2 and 5 after the meal. The total dose of glucagon released is approximately ³⁄₂₀₀ths of a unit over those three hours, this being sufficient to provide the patient with protection from hypoglycemia during his period of greatest susceptibility.

EXAMPLE 3

Co-administration of Glucagon Transdermally and Insulin for the Control of Diabetes and Prevention of Hypoglycemia [Including Patch and Topical Cream]

The use of transdermal patches for the delivery of therapeutic drugs is increasingly more common. Patches provide a non-invasive and easy method of delivering some drugs to the bloodstream. Nicotine and hormone replacement therapies are perhaps the best known uses of this technology. One of the characteristics of drug delivery by transdermal patch is that the rate of delivery is typically constant and persists for a long period of time (as long as the patch is worn). This characteristic has proven beneficial in the area of pain management (FENTANYL) and nicotine replacement therapy, in which long duration flat profiles are ideal. This characteristic makes the transdermal patch suitable for basal replacement of insulin or glucagon. See PCT patent publication No. WO0243566, incorporated herein by reference.

Figure 6:
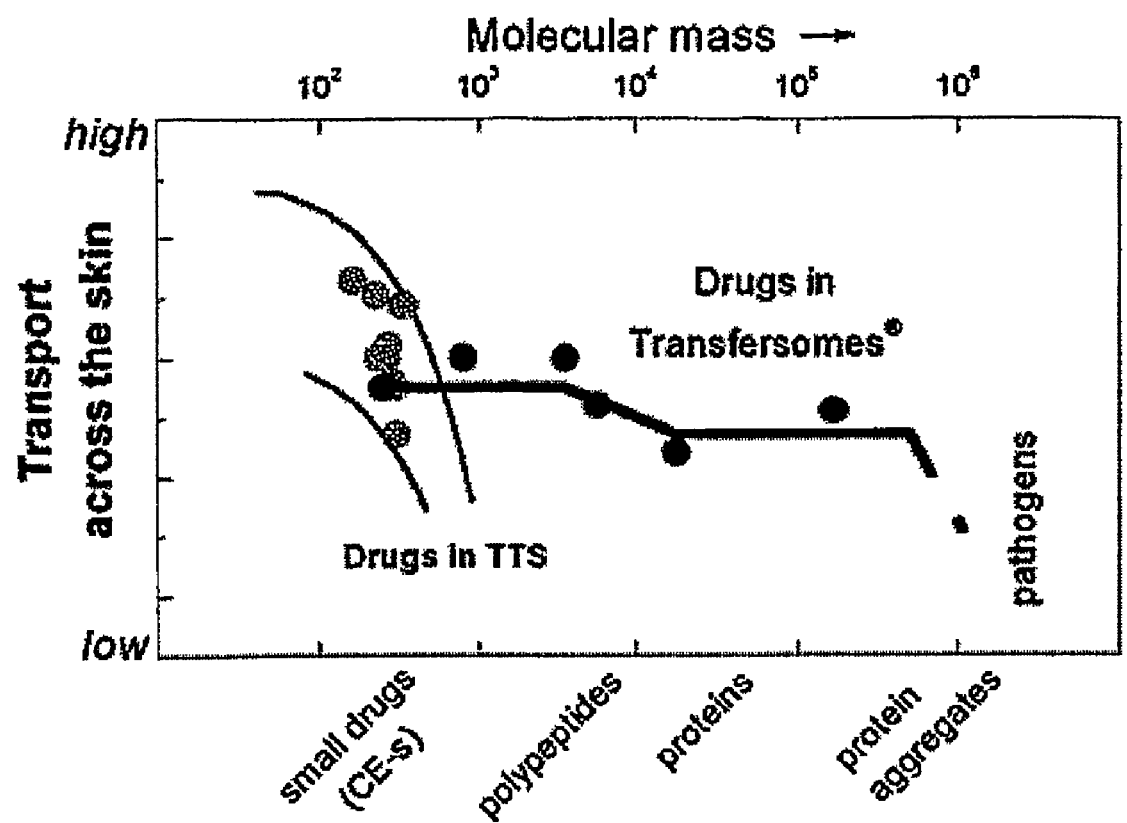
FIG. 6 illustrates the effect of molecular weight and lipophlicity on the rate of transdermal transport in case of permeation (upper and lower grey curve for the more or less lipophilic substances, respectively) or of the TRANSFEROME® mediated penetration (black line and bullets). Dotted black bullets represent the commercial drugs in transdermal patches.

Fast-acting patches are also known. The delivery of proteins (insulin in particular) transdermally into the bloodstream in well under an hour is reported in U.S. Pat. No. 5,707,641, incorporated herein by reference. The ability to deliver other proteins in the same way and using similar formulations is also recited. Glucagon can accordingly be administered in such a manner. Development of insulin patches is currently being pursued by Helix BioPharma, from Canada, and IDEA in Germany, where phase II trials are currently in progress. The IDEA technology (TRANSFEROMEs®) is directed to the transport of large molecules, such as peptides, across the dermal barrier. FIG. 6 illustrates the effect of molecular weight and lipophilicity on the rate of transdermal transport in case of permeation (upper and lower grey curve for the more or less lipophilic substances, respectively) or of the TRANSFEROME® mediated penetration (black line and bullets). Grey bullets represent the commercial drugs in transdermal patches. Regardless of the technology, the ability to efficiently transport peptides transdermally is proven and imminent. In particular, both insulin and glucagon can be delivered transdermally, thus enabling the invention to be practiced using transdermal patches and similar devices.

A variety of possible patch structures and matrices are envisaged according to the specific mode of use intended. For example, one can employ two basic types of insulin matrix, one for basal insulin replacement and one for prandial insulin replacement. Glucagon patches can be formulated to provide post-prandial glucagon for protection from hypoglycemia or basal glucagon replacement. The invention can be practiced using patch matrices comprising combinations of these basic types, either together in the same matrix or separately in sub-matrices.

Thus, the following patch matrices are useful in the practice of the invention:
- a matrix containing insulin for basal insulin replacement;
- a matrix containing insulin for prandial insulin replacement;
- a matrix containing glucagon for basal glucagon replacement;
- a matrix containing glucagon for post-prandial protection from hypoglycemia;
- a matrix containing insulin for prandial insulin replacement and glucagon for post-prandial protection from hypoglycemia;
- a matrix containing insulin and glucagon for basal replacement of both insulin and glucagon; and
- matrices which are composed of 2 or more sub-matrices, each sub matrix being one of the matrices described above.

Topical creams may be used as an alternative to use of a patch.

For prandial insulin matrices, short acting insulins such as LISPRO (HUMALOG) or ASPART (NOVOLOG) can be used. The prandial insulin matrix is typically applied at or at some time before mealtimes, according to its rapidity of onset. A prandial insulin patch which minimizes the time to onset can be used so that the patch is applied near to mealtimes. The time to onset depends on the insulin concentration and the nature of the formulation. For example, a simple wet-matrix of insulin has slower onset than an insulin patch formulated according to U.S. Pat. No. 5,707,641. Monomeric insulin will act faster and be more easily absorbed than larger clusters of insulin molecules, because molecular size impacts bioavailability from transdermal patches.

A number of different methods of managing the delivery of prandial insulin can be utilized in practice of the present invention. For example, patches of different concentrations can be used for fixed periods of time, and the concentration selected by the patient would depend on the amount of carbohydrate eaten. The duration for which the patch is worn could be fixed. The patch would not necessarily be exhausted on removal, i.e. it could deliver a fixed concentration throughout its use. As another example, single concentration prandial patches could be employed as follows. The time the patch is worn is varied according to the amount of carbohydrate eaten. The patch would not necessarily be exhausted on removal, i.e. it could deliver a fixed concentration throughout its use.

As another example, prandial patches containing fixed doses of insulin could be used. The advantage of a selfexhausting patch is that failure to remove them does not of itself carry the risk of hypoglycemia. Such a patch would be substantially exhausted on removal and the rate of infusion would be front loaded. In one embodiment, the prandial insulin patch used has a variable insulin concentration (appropriate to the amount of carbohydrate consumed), has a very rapid onset (preferably immediate but not more than one hour), is removed or deactivated after a fixed length of time (preferably from between 3 and 5 hours) and activated at (or no longer than one hour before) mealtimes. Prandial glucagon patches are applied at mealtimes or at some predetermined time after the meal according to the rapidity of onset associated with the patch. The rate of onset is determined both by the concentration of the glucagon used and the nature of the formulation used. For example, a simple wet-matrix of glucagon would be expected to have a slower onset than a glucagon patch formulated according to the techniques described in U.S. Pat. No. 5,707,641.

In one embodiment, the glucagon patch is designed so that peak output of glucagon is reached at some time between 2 and 5 hours after application. This patch is applied at mealtimes.

A number of different patch constructions can be used to practice the invention. These include:
- a patch containing a single matrix or set of sub-matrices in a single compartment;
- a patch containing 2 or more separate compartments each containing its own matrix or set of sub-matrices, the patch being activated or deactivated as a single unit; and
- a patch containing 2 more separate and independent compartments, each containing its own matrix or set of sub-matrices, in which each compartment is independently activated and deactivated.

Other patch configurations can be employed, and practice of the invention is not limited to the configurations described above.

A. Insulin Administered Transdermally [Including Patch and Topical Cream]

(i) Insulin Administered Transdermally [Including Patch and Topical Cream] and by Subcutaneous Injection In this example only prandial insulin and prandial glucagon are administered by transdermal patch. This can be achieved in a variety of ways, including: (i) use of a single matrix of glucagon and insulin admixed; (ii) use of a single compartment with two sub matrices, one containing insulin and the other containing glucagon; (iii) use of a single patch containing two compartments, one containing insulin and the other containing glucagon, both compartments being activated and deactivated simultaneously; and (iv) use of two separate patches (or two compartments in a unitary patch), one containing insulin and the other containing glucagon, each patch or compartment being independently activated and deactivated. Basal insulin is delivered parenterally as described in Example 1.A.i by subcutaneous injection of a long-acting insulin such as GLARGINE or ULTRALENTE. In one embodiment, method (i) is used (see Example 7). If different matrices are used to achieve the desired pharmacokinetics, then method (ii) or (iii) can be used. If the timing of insulin onset and glucagon onset is not matched, then method (iv) can be used.

In this illustrative example, method (ii) above is used. The user activates the prandial patch at mealtimes (or preferably within one hour before mealtimes), thereby activating both sub-matrices at the same time. If a fixed concentration patch is used, the user removes the patch after a period of time proportionate to the amount of carbohydrate ingested. If a variable concentration patch is used, then the user removes the patch after a fixed period of time, typically between 1 and 3 hours after eating. In one embodiment, fixed concentrations are used. In such an embodiment, the amount of glucagon administered can be increased with the amount of insulin administered.

(ii) Insulin Administered Transdermally [Including Patch and Topical Cream]

In this example, both the insulin and glucagon are administered transdermally. Two different types of patch (or independently actuated compartments) can be employed. One patch (or compartment) contains a matrix designed to replace basal insulin over a 24 hour period. The other patch (or independently controlled compartment) functions in the manner described in Example 3.A.i. In accordance with Example 3.A.i, a single patch (or compartment) containing both the prandial insulin and glucagon in separate sub-matrices with onset times appropriate to applying the prandial patch (or activating the prandial compartment) at (or near) mealtimes is used.

In one embodiment a unitary device containing four independently actuable compartments is used, one containing basal insulin, which is activated on application and left active for 24 hours, and the other 3 compartments containing the prandial insulin and glucagon in separate sub-matrices within the same compartment, each compartment being separately activated at mealtimes and deactivated at some time after the meal, the time of activation being proportional to the amount of carbohydrate consumed.

On beginning a meal (or at some time up to an hour before the meal), the patient activates one of these prandial compartments [e.g. by pulling away a hermetic plastic seal between the patch and the skin], a process which initiates the transdermal infusion of the insulin and glucagon. At some later time, a period in direct proportion to the amount of carbohydrate taken, the prandial compartment is deactivated [e.g. by replacing the barrier used to activate the compartment or the total removal of that compartment from the end of the patch]. The insulin formulation in the insulin sub-matrix is short acting insulin, and the patch is designed for rapid onset. The glucagon formulation in glucagon sub-matrix is designed to reach efficacious concentrations in the bloodstream between 1 and 3 hours after activation of the compartment, hence providing protection from hypoglycemia at the appropriate part of the cycle as described in Example 3.A.i.

In an alternative embodiment, a unitary device which allows for more than 3 meals a day may easily be devised by allowing for more than 3 prandial compartments. In an alternative embodiment, as described above, the prandial drugs may be contained in totally separate (and independently actuated) prandial patches. In an alternative embodiment, the prandial patch may consist of separate insulin and glucagon compartments so that each may be independently activated and deactivated.

A unitary device containing separate and independently controlled compartments for insulin and glucagon could have 7 separate compartments, one for basal insulin, 3 for prandial insulin, and 3 for prandial glucagon. The basal patch is designed to replace basal insulin (worn for 24 hours before being replaced). The insulin used may be any insulin suitable for transdermal delivery. The basal insulin compartment may also optionally contain an amount of glucagon (admixed or in a sub-matrix) sufficient to supply basal glucagon over each 24 hour period. This would have the beneficial effect of providing protection from hypoglycemia throughout the day and in particular during sleep.

B. Insulin Administered by Inhalation [Including Pulmonary, Buccal, Nasal and Sublingual]

In this example, insulin is delivered by inhalation as described in Example 4. This can involve inhalation only for the prandial insulin delivery (basal being delivered parenterally), or all insulin can be delivered by inhalation. The patient administers an amount of insulin appropriate to his meal by inhalation (in one or more actuations). He can optionally increase his insulin after a meal as appropriate.

The glucagon is administered by patch as described in Example 3.A.i. The patch (or set of glucagon compartments in a unitary patch) is attached to the skin, and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, as described in Example 5, the glucagon in the patch is a long acting glucagon (e.g. iodinated glucagon). The patch may then be worn for a shorter time while still ensuring that the protection afforded by the modified glucagon is provided over the required period of 2-5 hours.

In an alternative embodiment, the user can apply the glucagon by means of a transdermal cream, which acts similarly to a transdermal patch. The formulation of such a cream can differ from the formulation used in a patch but perform essentially the same function. When glucagon is administered in this way, it may be advantageous to encapsulate the glucagon in liposomes or TRANSFEROMEs® to prevent the supply of glucagon drying on the skin and reducing bioavailability.

C. Insulin Administered Parenterally

In accordance with Example 1.A.i, the patient's insulin needs are met by parenteral administration. The glucagon is administered by patch as described in Example 3.A.i. The patch (or set of glucagon compartments in a unitary patch) is attached to the skin and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, as described in Example 5, the glucagon in the patch is a long acting glucagon (e.g. iodinated glucagon). The patch may then be worn for a shorter time while still ensuring that the protection afforded by the modified glucagon is provided over the required period of 2-5 hours.

In an alternative embodiment, the user may apply the glucagon by means of a transdermal cream, which acts similarly to a transdermal patch. The formulation of such a cream can differ from the formulation used in a patch but performs essentially the same function. When glucagon is administered in this way, it may be advantageous to encapsulate the glucagon in liposomes or TRANSFEROMEs® to prevent the glucagon from drying on the skin and reducing bioavailability.

D. Insulin Administered by Pump

In this example, the patient's insulin needs are administered by pump as described in Example 2. The glucagon is administered by patch as described in Example 3.A.i. The patch (or set of glucagon compartments in a unitary patch) is attached to the skin and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, as described in Example 5, the glucagon in the patch is a long acting glucagon (e.g. iodinated glucagon). The patch may then be worn for a shorter time while still ensuring that the protection afforded by the modified glucagon is provided over the required period of 2-5 hours.

In an alternative embodiment, the user may apply the glucagon by means of a transdermal cream, which acts similarly to a transdermal patch. The formulation of such a cream may differ from the formulation used in a patch but performs essentially the same function. When glucagon is administered in this way, it may be advantageous to encapsulate the glucagon in liposomes or TRANSFEROMEs® to prevent the glucagon from drying on the skin and reducing bioavailability.

EXAMPLE 4

Co-administration of Glucagon by Inhalation and Insulin for the Control of Diabetes and Prevention of Hypoglycemia [Including Pulmonary, Buccal, Nasal and Sublingual]

A number of dry powder inhalation technologies are currently in development, including: Aradigm's AERx®, Inhale Therapeutics' Exubera®, Alkermes' and Eli Lilly's AIR, Insulin Technospheres (Mannkind/PDC), and Aerogen's and Disetronic's Aerodose. Methods and devices for delivering insulin to the pulmonary alveoli, where it may be absorbed into the blood stream, are described in U.S. Pat. Nos. 5,997, 848; 6,131,567; 6,024,090; 5,970,973; 5,672,581; 5,660,166; 5,404,871; and 5,450,336. The main difficulties that had to be overcome to enable aerosol macromolecular delivery were: low system efficiency (bioavailability); low drug mass per inhalation (c.f. asthma); and poor dosing reproducibility.

Perhaps the most important of these is efficiency (bioavailability). Bioavailability depends primarily on the aerosol particle size (most existing systems only deliver 10%-20% of the drug administered to the alveoli) rather than on the nature of the drug being administered. When the drug being delivered actually reaches the alveoli, its bioavailability is then very high almost regardless of the drug in question. Because the technical problems (and solutions) associated with delivering insulin are similar to those for delivering glucagon, the solutions enabling delivery of insulin are directly applicable to similarly sized macromolecules like glucagon. The present invention provides dry powdered formulations prepared by admixing insulin and glucagon. The use of inhalers for delivering insulin is primarily aimed at supplying rapid insulins for prandial purposes. Long acting insulins can be delivered by inhalation if desired.

The invention can be practiced using inhalers in a number of ways, including with insulin and glucagon in separate inhalers; with insulin and glucagon admixed in a fixed ratio in an inhaler; with a dual chamber inhaler in which insulin and glucagon are administered separately; and with dual chamber inhalers in which insulin and glucagon are administered simultaneously. Because prandial inhalers typically contain rapid acting insulins, they are unsuitable (in the way that insulin pumps are) for the delivery of basal insulin. A separate pump or chamber is provided in accordance with the invention if both prandial and basal insulins are to be delivered by inhalation.

A. Insulin Administered by Inhalation [Including Pulmonary, Buccal, Nasal and Sublingual]

The hypothetical patient administers basal insulin using ULTRALENTE by subcutaneous injections at a dosage level of 20 units administered at bedtime. Alternatively, he may choose to administer the same drug (in a dose that would provide a daily bioavailability of 20 units) by inhalation. It may also be beneficial or desirable for him to administer the basal dose by inhaler at a number of times during the day, for example, at mealtimes in addition to bedtime. Because there is a slight delay (approximately 20 minutes) before insulin attains significant serum concentration when compared to subcutaneous delivery, the user will administer his prandial insulin requirement approximately 20 minutes before eating. He does this by administering between 25 and 50 units (assuming a bioavailability of approximately 20%) of insulin by means of a metered dose inhaler.

The inhaler may be dose alterable (see U.S. Pat. Nos. 5,970,973; 5,672,581; 5,660,166; 5,404,871; and 5,450,336) or similar to currently used asthmatic devices, which deliver fixed and preset doses on each actuation. Whichever type is used, it may be desirable to administer the insulin in multiple actuations. By so doing, the patient can tailor his intake according to the amount of carbohydrate he actually consumes, rather than the amount he expects to eat, by "topping up" his dose at some time after beginning the meal. Furthermore, the more actuations used to administer the insulin, the better the corresponding dose reliability (reproducibility), because inhalation administration tends to vary from actuation to actuation, and multiple actuation delivery has an averaging or smoothing effect.

To prevent hypoglycemia associated with using inhaled insulin from occurring between 2 and 5 hours after eating, the glucagon inhaler is used to administer a dose equivalent to ½₀₀th of a unit of glucagon per hour parenterally between hours 2 and 5 following the meal. In one embodiment, a different inhaler for each type of insulin and glucagon is used. In one embodiment, a unitary inhaler with at least 2 drug chambers (for prandial insulin, glucagon and optionally basal insulin) and capable of independent actuation is used.

B. Insulin Administered Parenterally

In accordance with Example 1.A.i, the patient administers his basal and prandial insulin parenterally. Because the risk of hypoglycemia associated with using LISPRO insulin typically occurs between 2 and 5 hours after eating, the glucagon inhaler is used to administer a dose equivalent to ½₀₀th of a unit of glucagon per hour parenterally between hours 2 and 5 following the meal. Alternatively, a modified glucagon of long-acting duration (e.g. iodinated glucagon) with delayed onset is used in the glucagon inhaler and administered at mealtimes with the prandial insulin.

C. Insulin Administered by Pump

In accordance with Example 2.A, basal and prandial insulin are delivered by pump. The risk of hypoglycemia arises after 2 to 3 hours, and so the patient administers glucagon by inhaler 2 hours after eating. He administers one puff from a metered dose inhaler at hours 2, 3 and 4, thus providing protection during the period of susceptibility. The dose per actuation corresponds to ½₀₀th of a unit of glucagon administered parenterally. Alternatively, a modified glucagon of long-acting duration (e.g. iodinated glucagon) with delayed onset is used in the glucagon inhaler and administered at mealtimes with the prandial insulin.

D. Insulin Administered Transdermally [Including Patch and Topical Cream]

In accordance with Example 3.A.ii, the patient administers his insulin (both basal and prandial) by transdermal patch or by topical cream. The risk of hypoglycemia arises after 2 to 3 hours, and so the patient administers glucagon by inhaler 2 hours after eating. He administers one puff from a metered dose inhaler at hours 2, 3 and 4, thus providing protection during the period of susceptibility. The dose per actuation corresponds to ½₀₀th of a unit of glucagon administered parenterally. Alternatively, a modified glucagon of long-acting duration (e.g. iodinated glucagon) with delayed onset is used in the glucagon inhaler and administered at mealtimes with the prandial insulin.

EXAMPLE 5

Co-administration of Glucagon and Insulin, Admixed and Parenterally for the Control of Diabetes and Prevention of Hypoglycemia In Example 1, the insulin and glucagon were administered parenterally and separately. In one embodiment of the invention, the two drugs are administered simultaneously an admixed form. Insulin and glucagon may be admixed with little if any interaction or degradation of either product. In non-diabetics, it is typically found that following the increased insulin output after a meal of carbohydrate there is an associated increase in glucagon output (actually a restoration of output following the initial depression of glucagon output due to the initial gut-induced rise in blood sugar after the ingestion of carbohydrate). This pattern of insulin production followed by glucagon production assumes a relatively fixed relationship.

To ensure that the glucagon provides protection over the period required, one can increase the amount of the glucagon component in the admixture so that it is present in the required concentrations when desired (to prevent hypoglycemia between 2 and 5 hours after the meal), or one can use a glucagon formulation with delayed onset. One formulation of glucagon provided by the invention has both a delayed release and an extended release [e.g. delayed by 2 to 3 hours and releasing over approximately 3 hours].

There are a variety of technologies known to those skilled in the art for modifying the release and/or pharmacokinetic characteristics of proteins, including modification of the amino acid sequence at the site corresponding to the metabolic deactivation point associated with the protein, "pegylation" or PEG-modification of the protein (see, for example, PCT Patent publication Nos. WO0232957, WO9831383, and WO9724440, EP patent publication Nos. EP0816381 and EP0442724, and U.S. Patent Publication Nos. 2002/0115592; U.S. Pat. Nos. 5,234,903; and 6,284,727); other polymer encapsulations (see EP patent publication No. EP0684044); lipophilic modification (see U.S. Pat. Nos. 5,359,030; 6,239, 107; 5,869,602; and 2001/0016643; EP patent publication No. EP1264837; and PCT Patent publication Nos. WO9808871 and WO9943708; formulating into liposomes (see U.S. Pat. Nos. 6,348,214 and 6,197,333); serum albumin modification (see PCT Patent publication Nos. WO02066511 and WO0246227 and U.S. Pat. No. 4,492,684); formulating in the form of emulsions, microspheres, microemulsions, nanoencapsulation and microbeads (see U.S. Pat. Nos. 4,492, 684; 5,445,832; 6,191,105; 6,217,893; 5,643,604; 5,643,607;

and 5,637,568); formulations involving ligands (see PCT Patent publication No. WO0222154); and iodination (see U.S. Pat. No. 3,897,551).

In this example, an iodination method of increasing half life (as described in U.S. Pat. No. 3,897,551; see form I3G) is employed. Iodinated glucagon has extended activity (measured in terms of elevated glucose levels) of between 1 and 3 hours, depending on the extent of iodination. In one embodiment LISPRO insulin and I3Glucagon are admixed so that the modified glucagon is present at approximately 1.5% by weight of the insulin in the mixture (keeping the concentration of insulin per ml in our LISPRO formulation constant). Because of the longer lasting effect of the modified glucagon, a smaller proportion of glucagon to insulin by weight will be required.

The hypothetical patient then administers between 5 and 10 units (measured in terms of the insulin contained therein) of the insulin-glucagon formulation at mealtimes in the standard way. In so doing, he administers between 3/800ths and 3/400ths of a unit of modified glucagon. Given the longer action of the modified glucagon, this provides (assuming the modified glucagon has for example twice the effect on glucose levels compared to standard glucagon) the same protection as described in Example 1.A. The glucagon so administered will be efficacious continuously between hours 2 and 5 as required.

EXAMPLE 6

Co-administration of Glucagon and Insulin, Admixed, by Pump for the Control of Diabetes and Prevention of Hypoglycemia The method of the invention may also be practiced using pump-based administration of an admixture of both insulin and glucagon. This method provides protection from hypoglycemia in direct proportion to the amount insulin used and with a built in delay. It also replaces basal levels of glucagon throughout the day and especially after meals, as it will also be administered with the basal insulin administered by the pump. In this embodiment, the invention can be practiced using standard pumps currently available and described in Example 2. The only difference is that the insulin cartridges used will contain a mixture of insulin and glucagon (optionally modified release glucagon), with the glucagon component being between 0.1 and 5% (preferably between 0.5 and 3%), and typically 1.5% by weight compared to the insulin component.

Figure 7:
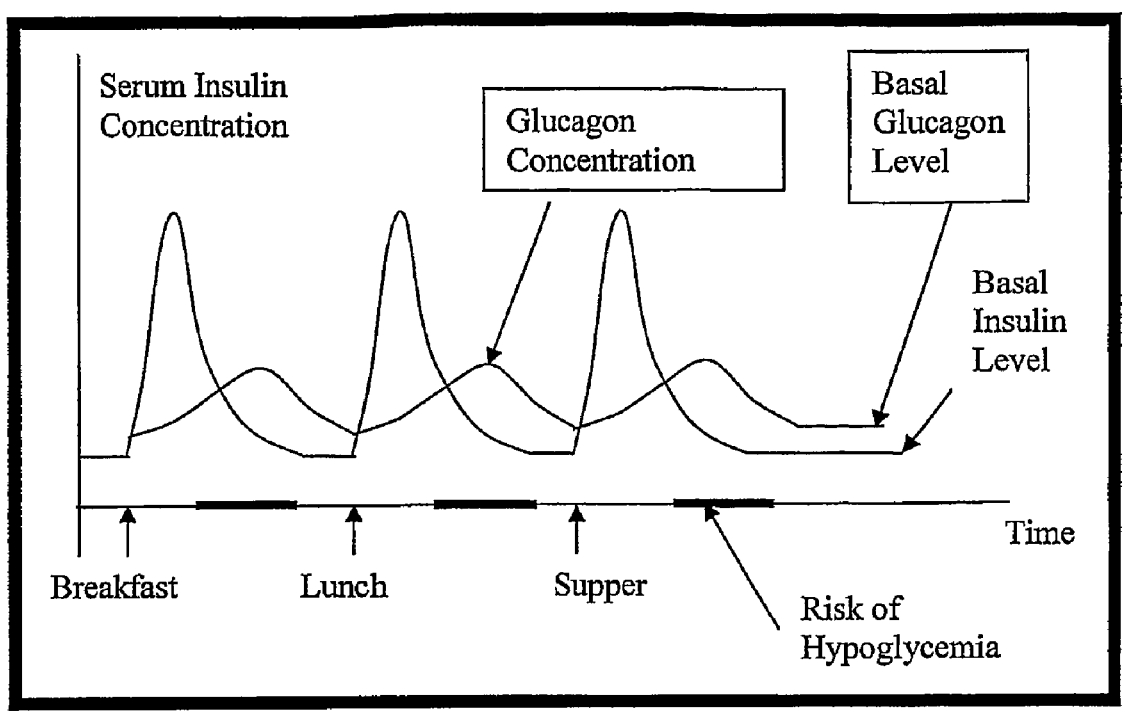
FIG. 7 is a graph illustrating the insulin and glucagon profiles of a hypothetical patient, as described in Example 6, showing for both drugs a very simple, flat line graph (basal insulin and glucagon infusions) punctuated by peaks (corresponding to prandial insulin and glucagon infusions) that would pertain when glucagon and insulin are administered in an admixed formulation.

The insulin/glucagon mixture is then administered by pump (for both basal and prandial insulin). The resulting glucagon (modified glucagon) plasma concentrations will map onto the insulin profile but with the attenuating characteristics of the glucagon variant used. This is illustrated in FIG. 7. This method will provide protection from hypoglycemia over the period of susceptibility as required. In one embodiment, the pump is equipped with a glucose sensor (see U.S. Pat. No. 5,474,552).

EXAMPLE 7

Co-administration of Glucagon and Insulin, Admixed, Transdermally for the Control of Diabetes and Prevention of Hypoglycemia [Including Patch and Topical Cream]

In this example, both the insulin and glucagon are administered by transdermal delivery. The prandial insulin and glucagon are admixed in the same matrix or cream. Two different types of patch (or independently actuated compartments) can be employed. One patch (or compartment) will contain a matrix designed to replace basal insulin over a 24 hour period. The other patch (or independently controlled compartment) functions in the manner described in Example 3.A.i and provides prandial glucagon and insulin in a single matrix. The onset times of the glucagon and insulin are matched so that when the patch is actuated, insulin reaches efficacious plasma levels very quickly whereas the glucagon only reaches efficacious levels after 2-3 hours. The patch is applied at mealtimes and preferably no more than one hour before the meal.

In one embodiment, a unitary device containing four independently actuable compartments is used, one containing basal insulin, which is activated on application and left active for 24 hours, and the other 3 compartments containing the prandial insulin and glucagon in the same matrix, each compartment being separately activated at (or near) mealtimes and deactivated at some time after the meal, the time of activation being proportional to the amount of carbohydrate consumed. On beginning a meal (or up to an hour before the meal), the patient activates one of these prandial compartments [e.g. by pulling away a hermetic plastic seal between the patch and the skin], a process which initiates the transdermal infusion of the admixed insulin and glucagon. At some later time, a period in direct proportion to the amount of carbohydrate taken, the prandial compartment is deactivated [e.g. by replacing the barrier used to activate the compartment or the total removal of that compartment from the end of the patch].

The combined insulin and glucagon formulation in the prandial compartment contains short acting insulin, and the patch is designed for rapid onset of the insulin. The glucagon component is designed to reach efficacious concentrations in the bloodstream between 1 and 3 hours after activation of the compartment, hence providing protection from hypoglycemia at the appropriate part of the cycle as described in Example 3.A.i.

In an alternative embodiment, a unitary device which allows for more than 3 meals a day can be used and contains more than 3 prandial compartments. The basal patch is designed to replace basal insulin (worn for 24 hours before being replaced). The insulin used may be any insulin suitable for transdermal delivery. It may be advantageous to use intermediate duration insulin in preference to short-acting insulin so that any variation in insulin absorption over the lifetime of the patch would be minimized by the relatively long lifetimes of the insulin involved. The basal insulin compartment may also optionally contain an amount of glucagon (admixed) sufficient to supply basal glucagon over each 24 hour period. This would have the beneficial effect of providing protection from hypoglycemia throughout the day and in particular during sleep.

EXAMPLE 8

Co-administration of Glucagon and Insulin, Admixed, by Inhalation for the Control of Diabetes and Prevention of Hypoglycemia [Including Pulmonary, Buccal, Nasal and Sublingual Delivery]

The present invention provides methods and pharmaceutical formulations for delivery of glucagon admixed with insulin by inhalation. In this example, a long acting glucagon (such as, for example, iodinated glucagon as described in U.S. Pat. No. 3,897,551, e.g. I2G) is admixed with LISPRO insulin and delivered by a typical insulin inhaler (e.g. as disclosed in U.S. Pat. No. 5,970,973). Basal insulin may be delivered in the standard way by subcutaneous injection, as described in Example 1A, or it may be delivered by inhaler. Glucagon may optionally be included in this formulation in an extended release formulation if desired to provide basal glucagon replacement.

The insulin powder used is admixed with the modified glucagon so that the modified glucagon content is between 0.1% and 5% (preferably between 0.5% and 3%), and typically 1.5% by weight compared to the insulin. In this embodiment, the modified glucagon bioavailability is estimated to be the same as that of the insulin used. If the particular formulation used results in a different bioavailability, the glucagon fraction will be increased or decreased accordingly. The patient will administer the combined insulin and glucagon at mealtimes to provide systemic insulin equivalent to between 5 and 10 units. Assuming bioavailability of approximately 20%, this involves administering between 25 and 50 units of insulin and between about 3/400th and 3/800th of a unit of modified glucagon.

EXAMPLE 9

Co-administration of Glucagon and Insulin, Orally, for the Control of Diabetes and Prevention of Hypoglycemia The delivery of large molecules (e.g. proteins) orally is well known in the art. Typically this involves enteric administration (see U.S. Pat. No. 5,641,515). In accordance with the teachings of the present invention, similar methods are used to deliver glucagon orally. In a typical scenario involving the oral delivery of a mixture of insulin and glucagon, the patient takes an enteric tablet containing insulin appropriate to his prandial up to an hour before eating. The insulin component is designed for rapid onset once it begins release. The glucagon component is designed to release later than the insulin component, preferably by 2-3 hours. Optionally, modified glucagon with a long half life may be used to ensure that glucagon levels are elevated over an extended period. Administered in this way, the glucagon will be correctly and appropriately timed to provide protection from hypoglycemia. In another embodiment, the patient administers his insulin using any of the methods described herein and administers a glucagon pill as required, for example, with each of his meals, to prevent hypoglycemia.

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. A method of reducing the risk of hypoglycemia in a diabetes patient who is being treated with insulin or an insulin secretagogue, which method comprises administering to the patient an amount of glucagon that results in a plasma glucagon level in the range achieved by intravenous infusion of glucagon at a rate that is not less than 0.10 ng/kg/min and not more than 5.00 ng/kglmin, wherein glucagon is administered daily as part of a diabetes treatment regimen, and wherein said patient is not suffering hypoglycemic symptoms and has a blood glucose level of from 70-110 mg/dL when said glucagon is administered.

2. The method of claim 1, wherein said glucagon is contained in a device that controls administration of the drug to a patient.

3. The method of claim 2 wherein the device is a pump.

4. The method of claim 3 wherein the pump is programmed to deliver glucagon daily.

5. The method of claim 3 wherein the pump is programmed to administer glucagon is administered within four hours after said patient has last been administered insulin.

6. The method of claim 2 wherein the device is a transdermal delivery device.

7. The method of claim 1, wherein both insulin and glucagon are administered parenterally.

8. The method of claim 1 wherein the secretagogue is a sulfonylurea.

9. The method of claim 8 wherein the secretagogue is acetohexamide, chlorpropamide, tolazamide, tolbutamide, glimepiride, glipizide, or glyburide.

10. The method of claim 1 wherein the secretagogue is a meglitinide.

11. The method of claim 10 wherein the secretagogue is nateglinide or repaglinide.

12. The method of claim 1 wherein glucagon is administered daily at bedtime.

13. The method of claim 7 wherein the patient is unable to sense low blood glucose accurately due to hypoglycemic unawareness.

* * * * *